United States Patent [19]
Buelna

[11] Patent Number: 5,632,752
[45] Date of Patent: *May 27, 1997

[54] SURGICAL SUTURING DEVICE

[75] Inventor: Terry Buelna, Laguna Beach, Calif.

[73] Assignee: Urohealth Systems, Inc., Costa Mesa, Calif.

[ * ] Notice: The term of this patent shall not extend beyond the expiration date of Pat. No. 5,468,251.

[21] Appl. No.: 279,367

[22] Filed: Jul. 22, 1994

Related U.S. Application Data

[63] Continuation-in-part of Ser. No. 134,561, Oct. 22, 1993, Pat. No. 5,468,251.

[51] Int. Cl.$^6$ ............................................. A61B 17/00
[52] U.S. Cl. ...................... 606/144; 606/139; 606/222; 112/169
[58] Field of Search ........................... 606/139, 144, 606/145, 147, 148, 151, 222–224; 112/169, 80.03, 222; 206/380; 163/5; 223/102–104

[56] References Cited

U.S. PATENT DOCUMENTS

| | | | |
|---|---|---|---|
| 29,648 | 8/1860 | Drake | 112/222 |
| 818,152 | 4/1906 | Edwards. | |
| 2,516,710 | 7/1950 | Mascolo. | |
| 4,527,564 | 7/1985 | Eguchi et al.. | |
| 5,037,433 | 8/1991 | Wilk et al. | 606/139 |
| 5,152,769 | 10/1992 | Baber | 606/145 |
| 5,306,280 | 4/1994 | Bregen et al. | 606/139 |
| 5,336,239 | 8/1994 | Gimpelson | 606/223 |
| 5,374,275 | 12/1994 | Bradley et al. | 606/148 |
| 5,403,329 | 4/1995 | Hinchcliffe et al. | 606/139 |
| 5,439,469 | 8/1995 | Heaven et al. | 112/169 |

FOREIGN PATENT DOCUMENTS

| | | |
|---|---|---|
| 3639489 | 5/1988 | Germany. |
| 166102 | 11/1964 | U.S.S.R.. |
| 1319836 | 6/1987 | U.S.S.R.. |
| 1572613 | 6/1990 | U.S.S.R.. |

OTHER PUBLICATIONS

REMA–Medizintechnik GmbH, "Innovation through Progress" 8 pages.
Product Brochure—The Endo Judge from Synergistic™, 2 pages.

*Primary Examiner*—Jeffrey A. Schmidt
*Attorney, Agent, or Firm*—Burns, Doane, Swecker & Mathis, L.L.P.

[57] ABSTRACT

An improved device and method for suturing penetrations and incisions through tissue into a body cavity. The device should find particular use in laparoscopic and other types of minimally invasive surgical procedures. A device according to the invention includes a shaft and an inverted needle joined to the shaft. Two ends of a length of suture material are attached at or near a sharpened proximal tip on the needle. The device may include a movable shield that is slidable to alternately cover and expose the sharpened tip of the needle. This shield may include a blunt distal end and an inclined proximal surface to assist the surgeon in guiding the hook into and out of the body cavity. The device may be provided with a visual and tactile indicator on one side of the device to assist the user in threading and removing the suture material into and out of a selected side of the hook.

26 Claims, 14 Drawing Sheets

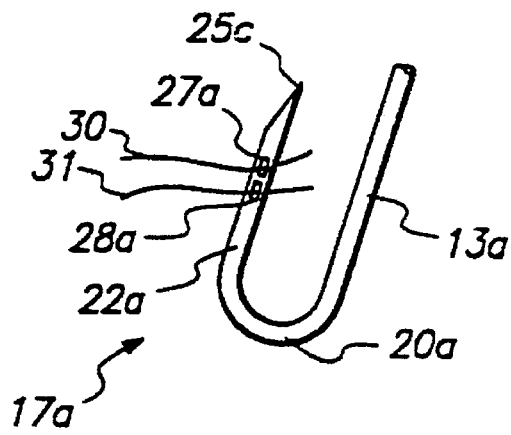
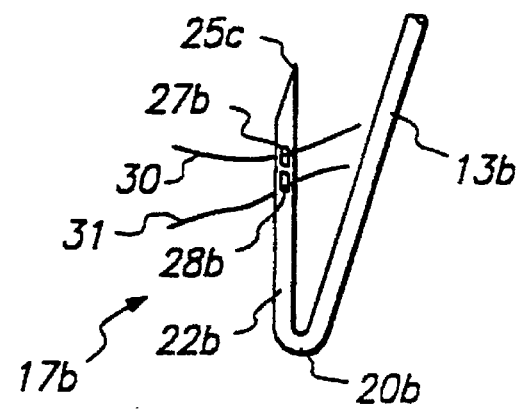
FIG. 1A         FIG. 1B
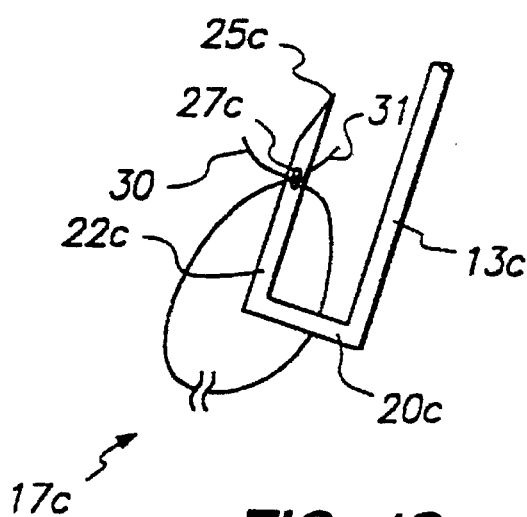
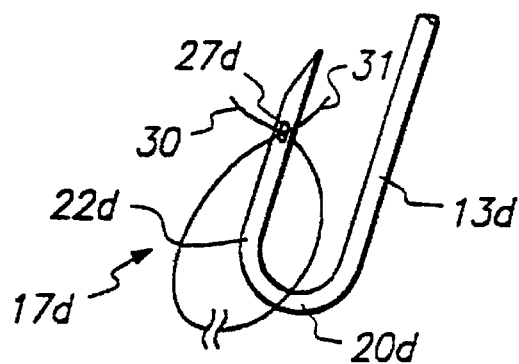
FIG. 1C         FIG. 1D

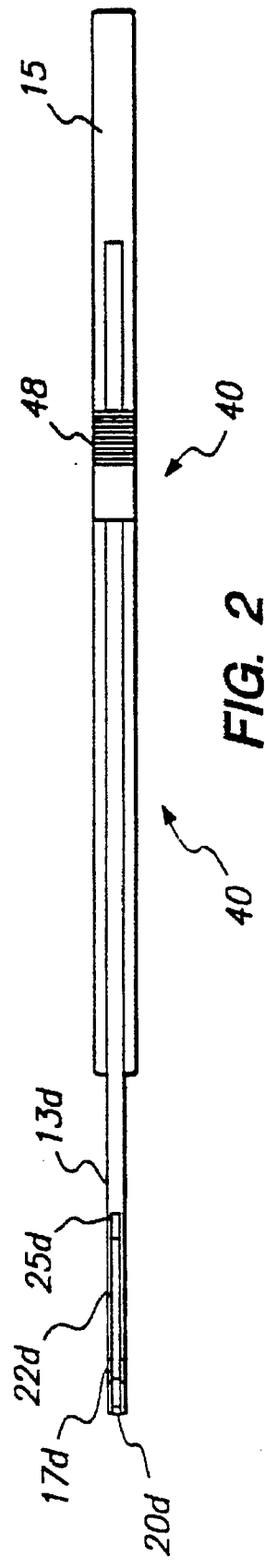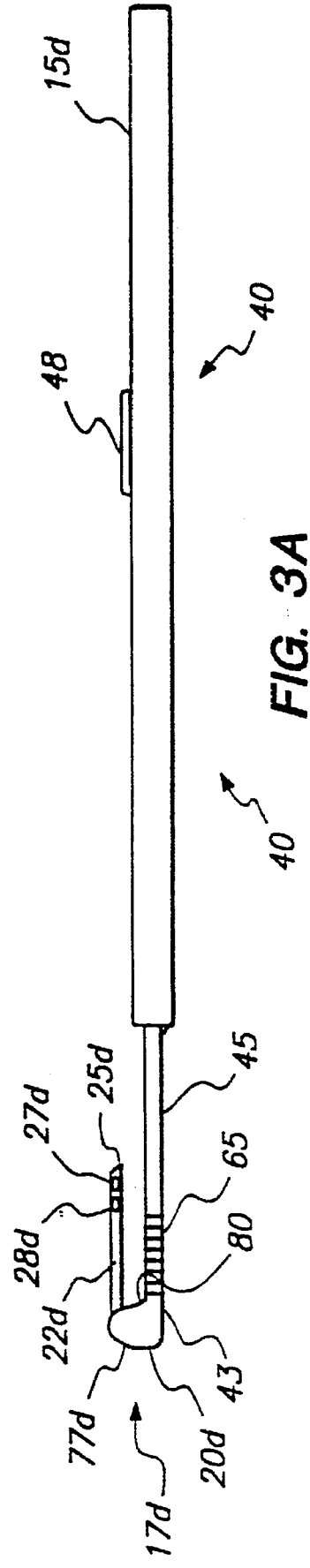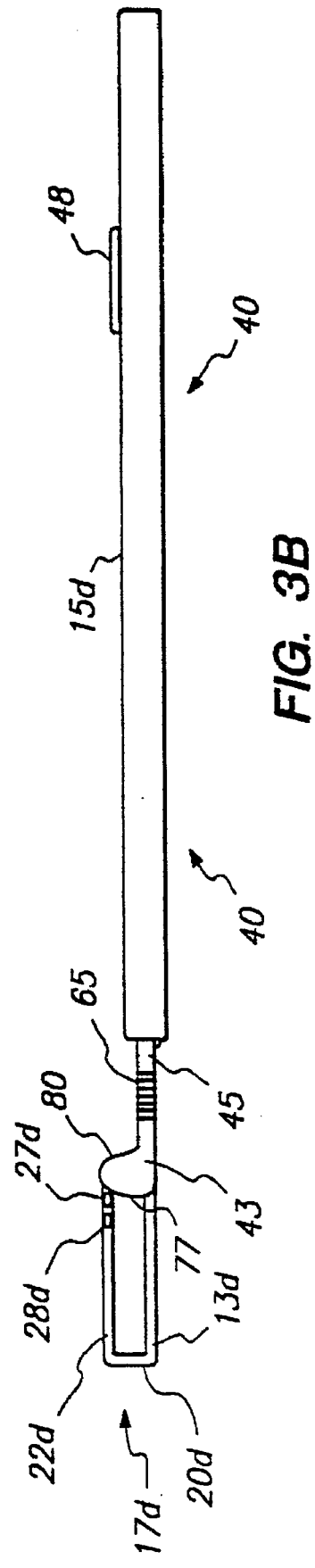

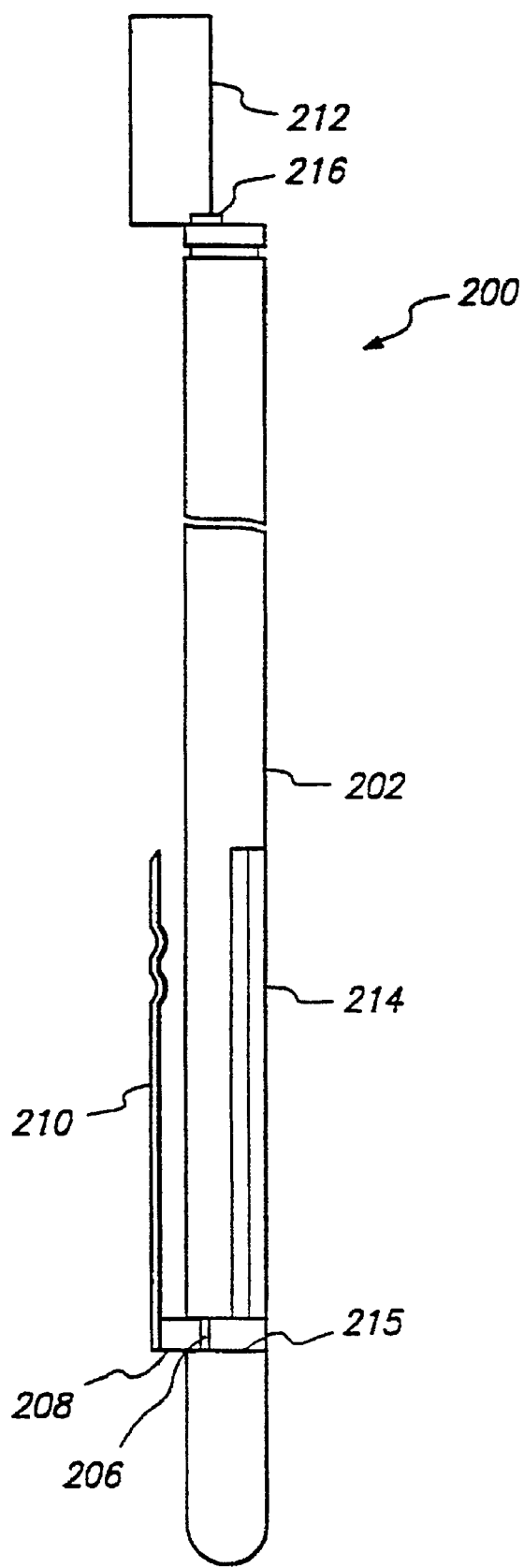
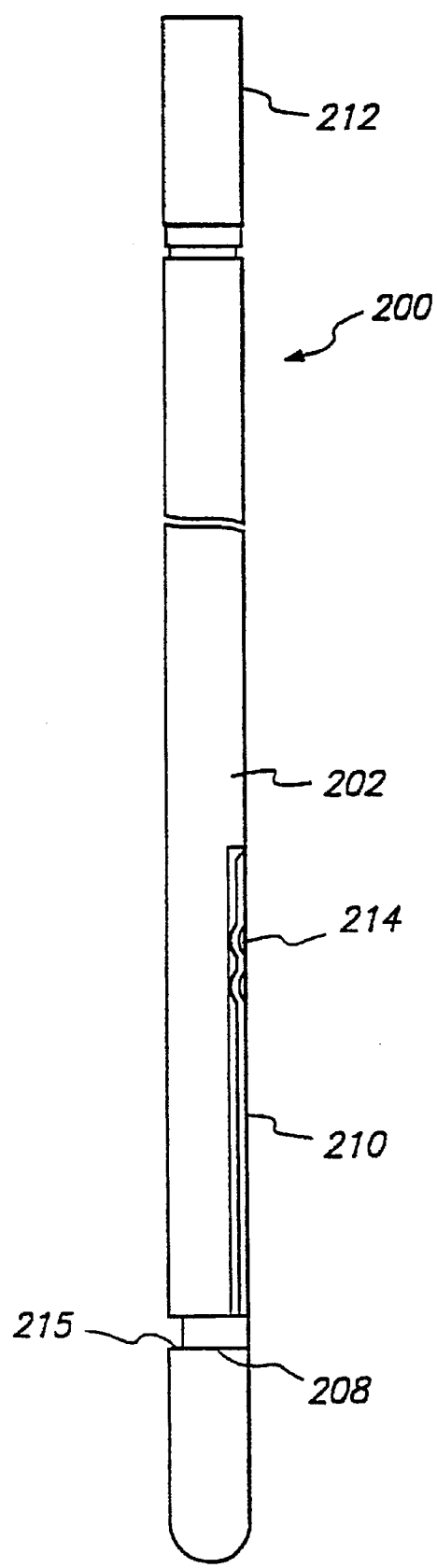

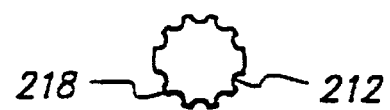
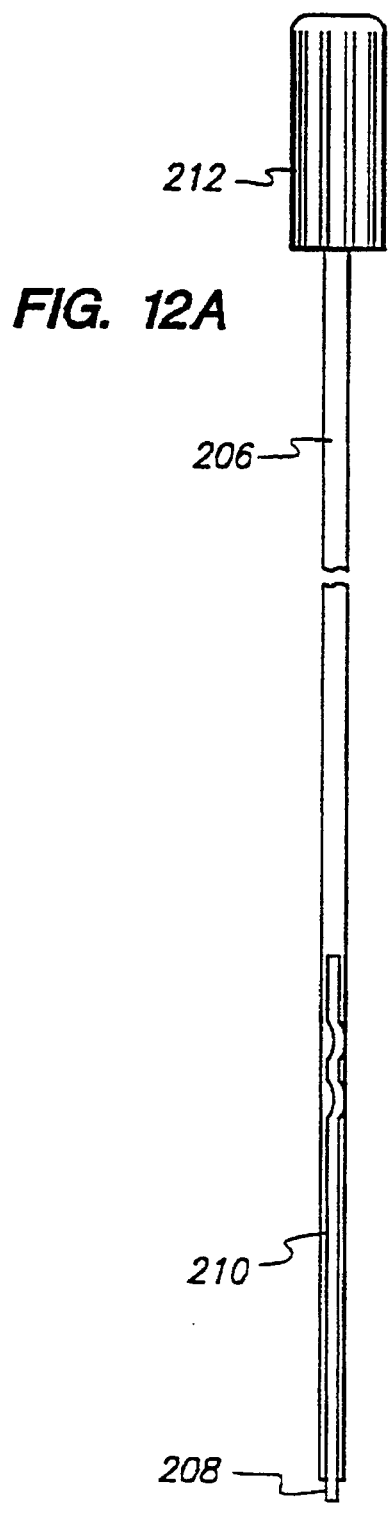
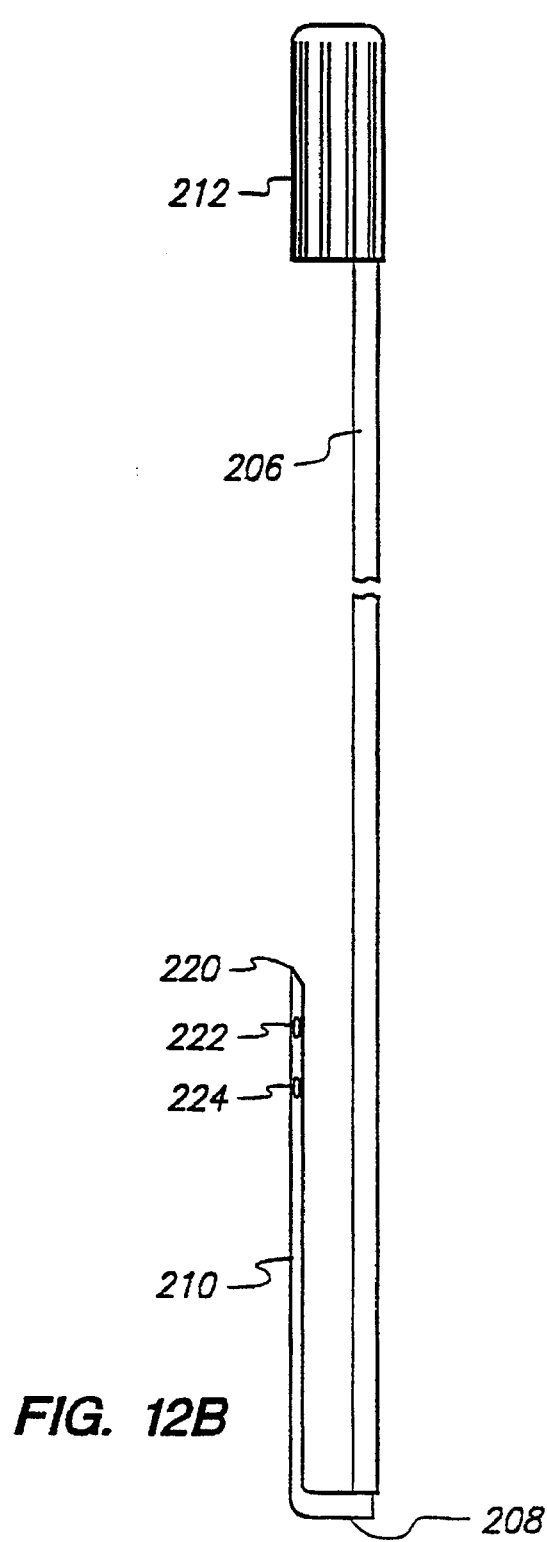

SURGICAL SUTURING DEVICE

CROSS-REFERENCE TO RELATED APPLICATIONS

This application is a continuation-in-part application of patent application Ser. No. 08/134,561 filed on Oct. 22, 1993 now U.S. Pat. 5,468,251. (Attorney Docket No. 14523-48).

BACKGROUND OF THE INVENTION

Field of the Invention

The invention relates generally to devices and methods for performing surgical procedures. More particularly, the invention provides a device and method for suturing closed an opening through tissue into a body cavity. The invention will find particular use in laparoscopic and other types of minimally invasive surgery.

Minimally invasive surgery, including laparoscopic, endoscopic, and arthroscopic surgery, is generally performed through small incisions using instruments specially adapted for these procedures. These techniques offer significant advantages over conventional "open" surgery techniques. In particular, trauma to the patient is greatly reduced and recovery times are significantly shorter. For these and other reasons, minimally invasive surgeries are often much less costly than corresponding conventional surgical techniques.

Incisions made while performing minimally invasive surgery can be very small (a few millimeters), or somewhat larger (a few centimeters). Currently, in laparoscopic procedures, incisions larger than about five millimeters are typically sutured closed after completion of the surgery to prevent herniation. Suturing of such small incisions is problematic, however, for the simple reason that the surgeon can not get his fingers and/or instruments into the incision to suture the incision in the conventional manner.

Suturing of such small incisions is difficult enough in thin patients, and even more difficult in overweight or obese patients. In these patients, the thick layer of fat underlying the skin makes it difficult to reach the fascia, a layer of tough, fibrous tissue through which the suture should be anchored. For these reasons, it would be advantageous to provide special tools and methods to facilitate suturing of surgical incisions made during minimally invasive surgeries.

An existing tool for suturing small incisions is called a Grice needle. This device is a long needle into which a suture can be threaded. The needle is pushed through the fascia on one side of the incision into the patient's body cavity. The suture is then retrieved using a second needle which is penetrated on the opposite side of the incision which has an integral suture snare. Although workable, the use of the Grice needle can be problematic in closing trocar penetrations made in laparoscopic and other minimally invasive procedures, particularly after the viewing scope has been removed. Problems can also arise when the Grice needles are used in blind procedures where the extent of needle penetration cannot be observed.

Another device for suturing percutaneous penetrations is described in a sales brochure published by Rema-Medizintechnik GmbH (Germany). The Rema "Deep Suture" device includes a handle, a control screw, and a shaft upon which a pair of special needles are mounted. Although operation is not clearly described, the device is apparently used by inserting the shaft through an incision and turning the control screw to deploy a pair of needles radially outward so that they lie on opposite sides of the penetration. The device is then hand lifted to penetrate the needles through the fascia from inside the body. The needles are then removed from the handle, and suture extending between the needles pulled and tied to close the penetration.

While perhaps offering some improvement over the Grice needle, the Rema device is less than ideal in some significant respects. First, the Rema device is complex and would be costly to produce. Second, the fixed positioning of the special needles on the shaft limits the surgeon's flexibility in placing sutures around the incision. Additionally, the needles are directed outward in a parallel fashion and exit through the skin. Thus, the surgeon is not able to suture the fascia while allowing the overlying tissue to heal without sutures. The device is likely too expensive to be disposable and must therefore be cleaned and carefully sterilized between uses. Adequate cleaning and sterilization of a surgical device, especially one having a number of recesses in which blood can collect, is often difficult to achieve.

For the reason noted above, it would be advantageous to provide an improved suturing device and method. Ideally, the improved device would be compact and of simple construction. The device should allow for flexibility in deployment, and in particular should allow the surgeon to suture the fascia layer and/or peritoneum in percutaneous penetrations without suturing the overlying tissue (thus providing a more secure suture with reduced scarring). It would be particularly advantageous if the improved device could be made sufficiently inexpensive to be disposable so that resterilization would not be required.

DESCRIPTION OF THE BACKGROUND ART

A surgical needle having a curved distal end is disclosed in U.S. Pat. No. 818,152. Curved and bent surgical needles are described in the following patents and published applications: U.S. Pat. Nos. 5,152,769; 5,037,433; 4,527,564; and 2,516,710; German Patentschrift 628038 and Offenlegungsschrift 36 39 489; French Patent 455640; and Russian patent publications 1572613, 1319836, and 166102. The Remo-Medizintechnik discussed above is described in a brochure entitled REMA-Innovation through Progress.

SUMMARY OF THE INVENTION

The present invention provides devices and methods for suturing penetrations and incisions made through tissue into body cavities, including percutaneous penetrations and penetrations made through the walls of internal body organs, lumens, and the like. The present invention is particularly useful in laparoscope and other minimally invasive surgical procedures where it may be used for suturing the fascia layer in percutaneous penetrations made for introducing surgical instruments, typically made by the introduction of trocars. The device and method will also be useful in laparoscopic and other endoscopic procedures where the device may be introduced through a trocar for suturing internal tissue target sites.

Devices according to the present invention will comprise an elongate shaft having a proximal end and a distal end, with an inverted needle attached to the distal end of the shaft having a sharpened proximal tip. By "inverted" it is meant that the needle will be pointed or directed toward the proximal end of the shaft, with preferred needles being generally straight (usually over at least 3 cm, and preferably over the proximal-most 4 cm) and usually parallel to the elongate shaft. It will be possible, however, to use needles which are not entirely straight and which deviate somewhat from the parallel orientation, so long as the needle is able to be introduced inwardly through a penetration or incision and thereafter drawn outwardly through the tissue according to the method of the present invention. By "sharpened," it is meant that the proximal tip is tapered, honed, inclined, angled, or otherwise formed to facilitate penetration of the needle through tissue.

The surgical suturing device will carry a length of suture on the needle near the sharpened proximal tip thereof. At least two points on the suture will be removably attached to the needle in a manner such that both ends of the suture may be separately removed from the needle. In this way, the needle can be used to sequentially introduce a first end of the suture through tissue on one side of the penetration and thereafter introduce the other end of the suture through tissue on another side of the penetration without having to withdraw the device from the tissue penetration for reloading. Such methods will be described in more detail below.

Both ends of the suture will be attached to the needle as close as practical to the sharpened proximal tip thereof. Typically, the suture attachment points will be within 5 mm of the proximal tip, preferably being within the 2 mm of the proximal tip and more preferably being within 1 mm of the proximal tip. By locating the suture near the sharpened proximal tip, the suture will be drawn outward through the tissue very shortly after the needle tip emerges therefrom. In this way, the length of the needle can be reduced and the risk of accidental injury from the needle be lessened.

A variety of anchors can be used for removably attaching the suture ends to the inverted needle. In the exemplary embodiments, apertures or "eyes" are provided in the body of the needle immediately distal to the sharpened proximal tip. In the simplest case a single aperture or eye is provided, where both ends of the suture are drawn through the eye, preferably in opposite directions so that removal of the first suture end will not dislodge the second suture end. Preferably, a pair axially spaced-apart apertures are provided, with one end of the suture passing through each aperture. The two apertures permits the suture ends to be oriented on the same side of the needle, facilitating manipulation by the physician. Other suitable anchors include slots, cleats, adhesives, fasteners, and combinations thereof.

The inverted needle may be attached to the elongate shaft in any manner which holds the needle in the desired orientation. Typically, the inverted needle will be fixedly attached to the shaft, but in certain circumstances, it may be possible to use a needle which is removably attached. In the first exemplary embodiment of the device of the present invention, the inverted needle is formed from a continuous length of needle stock, typically a narrow gage stainless steel rod, with a junction region formed at the distal end of the device. The junction region may have a J-shape, a V-shape, or any other geometry which provides for the desired orientation. In a second exemplary embodiment, the inverted needle comprises a separate needle assembly which is attached at the distal end of a generally straight shaft body. The needle assembly includes three segments, with a lateral segment joining the inverted needle segment to a first axial segment which is attached directly to the shaft. It will also be possible to stamp the needle from flat metal stock and form the needle from plastics using conventional fabrication techniques.

In a preferred aspect of the present invention, a shield is provided for selectively covering the sharpened needle tip. In particular, it is desirable to cover the needle tip after both ends of the suture have been penetrated through tissue and the device must be withdrawn through the initial penetration which is to be closed. By covering the sharpened proximal tip of the inverted needle, accidental needle penetration can be avoided. Optionally, the needle tip may also be covered while the device is being introduced inwardly through the tissue incision or penetration. An exemplary shield structure is mounted on the shaft to axially slide between a first position in which the sharpened tip is exposed and a second position in which the sharpened tip is covered. Preferably, the shield includes a proximal surface which is inclined or canted away from the shaft to facilitate withdrawal of the device through the tissue penetration when the shield is in its second position, and a curved or blunt distal surface to facilitate introduction of the device.

In another aspect of the present invention, the surgical suturing device is provided with the suture preattached to the inverted needle in the manner just described. Typically, the combination of surgical suturing device and suture will be sterilized and disposed within a sterile package, such as a sterilized pouch.

In another particular aspect of the present invention, the needle will be generally straight and preferably have a length in the range from about 1 cm to 8 cm, preferably from 3 cm to 5 cm. The needle will also be generally parallel and laterally spaced apart from the shaft, typically by a distance in the range from about 3 mm to 15 mm, preferably from 5 mm to 10 mm.

According to the method of the present invention, the suturing device is first inserted through the tissue penetration and positioned so that the sharpened proximal tip of the inverted needle is at a first target side on one side of the penetration. The inverted needle is then drawn outwardly through the tissue so that its proximal tip carrying the suture emerges therefrom. In the case of suturing the fascia layer in a percutaneous penetration, the needle will be drawn out through the tissue just above the fascia layer and within the region of the penetration which lies in the subcutaneous layer. After removing a first end of the suture from the inverted needle, the distal end of the device is passed back through the penetration and the sharpened proximal tip positioned at a second target side on another side of the penetration. The device is again drawn outwardly so that the needle carrying the suture passes through the tissue, emerging at a desired location. The second end of the suture is then removed from the needle, and the first and second suture ends may be secured to close the penetration, typically by tying or optionally using some clamp or other fastening means for securing.

After removing the second end of suture from the inverted needle, the device must be withdrawn from the tissue penetration. Typically, this will be achieved by retracting the device through the penetration a third time so that the needle is withdrawn from the posterior surface of the tissue being sutured. The entire device may then be withdrawn through the penetration, preferably with the needle being covered by the shield. The device could be withdrawn, however, in other ways. For example, by using a removable needle, the needle could be detached from the shaft after or concurrent with the removal of the second end of suture. The remainder of the device could then be withdrawn from the penetration without concern over accidental needle penetration.

In another exemplary embodiment of the present invention, a suture device having a needle that can be moved between a recessed and an exposed position is provided. According to this embodiment, the suture device has an elongate shaft with a proximal end and a distal end and an inverted needle with a distal end and a sharpened proximal tip. The suture device has means located on the needle immediately distal to the sharpened tip for separately securing opposite ends of a length of suture thereto. This configuration allows one end of the suture to be removed from the needle without dislodging the other end. This embodiment further includes means for securing the distal end of the needle to the distal end of the shaft and the needle radially outward from a protected position to an exposed position.

In one aspect of the suture device, the means for moving the needle between the protected and exposed positions includes a knob on the proximal end of the shaft, a rod attached to the knob, and an arm attached to the rod. With this configuration, the distal end of the needle is secured to the arm so that rotation of the knob moves the needle between the protected and exposed positions.

In another particular aspect, the suture device has means for locking the needle in the exposed position. The locking means includes a resilient button at the proximal end of the shaft. The button extends in a proximal axial direction above a distal end of the knob when the needle is in the exposed position. This configuration prevents further rotation of the knob, thereby locking the needle in the exposed position. The needle is unlocked by depressing the button to allow the knob to be rotated to the protected position.

The shaft of the suture device is provided with a longitudinal recess for protecting the needle when the needle is in the protected position. In one aspect, the rod is housed within the shaft and the needle is positioned outside the shaft. The arm is curved so that when the needle is in the protected position, the arm is substantially flush with the shaft. Alternatively, the arm is straight and the shaft includes a vertical recess at the distal end for receiving the arm when in the protected position.

The present invention provides an exemplary method for suturing a tissue puncture site. According to the method, a suture device is provided which has an elongate shaft and an inverted needle at a distal end of the elongate shaft. A length of suture is removably attached to the needle near a sharpened proximal tip on the needle. The distal end of the device is inserted through the puncture site while the needle is recessed within the elongate shaft. The needle is then moved from the recessed position to an exposed position so that the sharpened tip can be positioned at a first target site on one side of the puncture site. The needle is then drawn outward through the tissue and a first end of the suture is removed therefrom. The distal end of the device is then reinserted through the puncture site and the sharpened tip is positioned at a second target site on the opposite side of the puncture site. The needle is then drawn outward through the tissue and a second end of the suture is removed therefrom. Once removed, the first and second suture ends are secured to close the puncture site.

In another aspect of the method, the distal end of the device is reinserted through the puncture site after the second end of the suture has been removed from the needle. The needle is then retracted to the protected position, and the device is withdrawn outward through the puncture site.

In a further aspect of the method, the needle is locked when the needle is in the exposed position. Before the needle is retracted, the needle is unlocked. The needle is locked in the exposed position by providing a resilient button that proximally extends in an axial direction beyond a distal end of the knob when the knob is rotated. The needle is unlocked by depressing the button to allow the knob to be rotated.

Preferably, the method is used at a percutaneous puncture site, and the needle is drawn outward through the fascia layer and subcutaneous layer into the puncture site.

In another aspect of the method, the suture ends are secured within the puncture site beneath the skin. According to another aspect, the suture device is disposed in a trocar and the tissue puncture site is in an internal body structure. In a further aspect, the needle is visualized when deploying the needle from the recessed position to the exposed position, and when positioning the sharpened tip at the second target site.

The invention provides another exemplary method for suturing a tissue puncture site. According to the method a suture device is provided having an elongate shaft and an inverted needle at a distal end of the elongate shaft. The needle includes an aperture near a proximal sharpened tip for receiving a length of suture having a first end and a second end. Initially, the distal end of the device is inserted through the puncture site while the needle is recessed within the elongate shaft. The needle is then moved laterally outward from the recessed position to an exposed position, and the sharpened tip is positioned at a first target site on one side of the puncture site. The needle is then drawn outward through the tissue and one of suture ends is directed through the aperture to load the suture on the needle. With the needle loaded, the distal end of the device is reinserted through the puncture site and the sharpened tip is positioned at a second target site on another side of the puncture site. The needle is then drawn outward through the tissue and the suture is removed from the needle. The first and second suture ends are then secured to close the puncture site.

In another aspect of the method, the distal end of the device is reinserted through the puncture site after the second end of the suture has been removed from the needle. The needle is then moved laterally outward to the recessed position where the distal end of the device is withdrawn outward through the puncture site.

BRIEF DESCRIPTION OF THE DRAWINGS

FIGS. 1A–1D illustrate alternative distal constructions of a first embodiment of a suturing device constructed according to the present invention;

FIG. 2 is a top view of a more advanced embodiment of the suturing device;

FIG. 3A provides a side view of the device of FIG. 2 with a needle shield extended;

FIG. 3B provides a side view of the device of FIG. 2 with the needle shield of FIG. 3A retracted.

FIGS. 11A and 11B illustrate an exemplary embodiment of a suturing device constructed according to the present invention.

FIGS. 12A–12C illustrate a knob, a rod, and a needle used to construct the suturing device of FIGS. 11A and 11B.

DESCRIPTION OF SPECIFIC EMBODIMENTS

Figure 5:
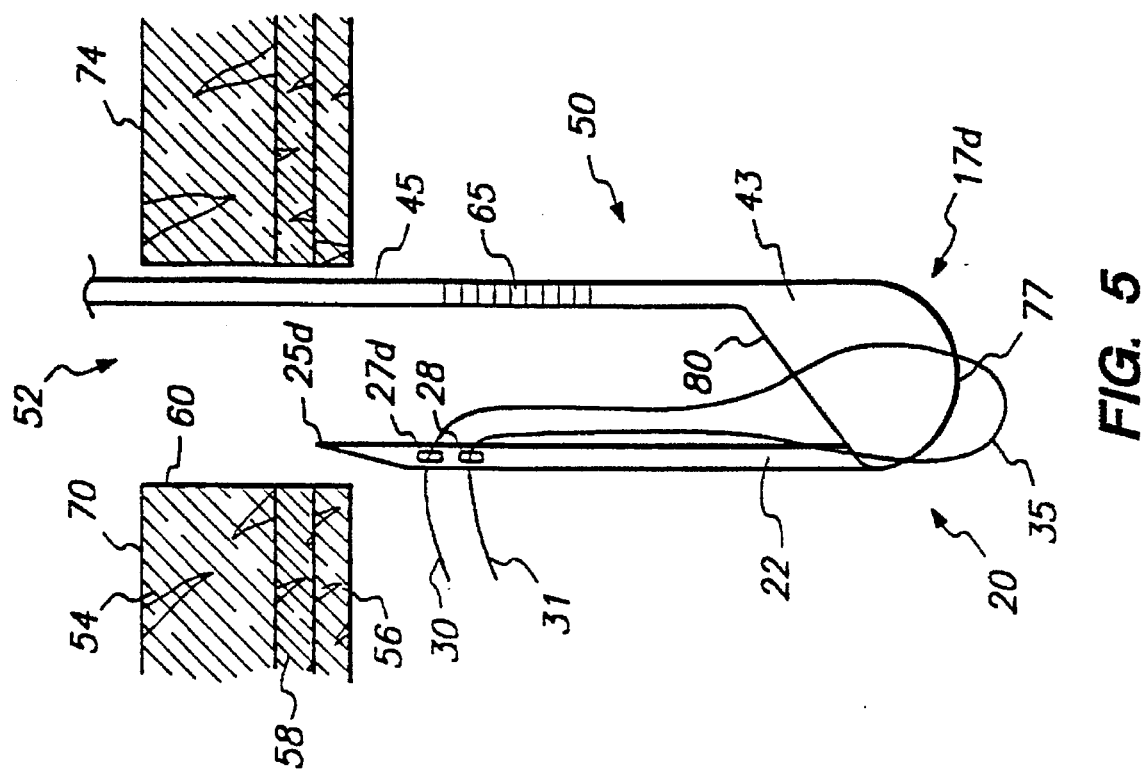
FIGS. 4–9 illustrate use of the device of FIGS. 2, 3A and 3B in an exemplary method for using the device according to the present invention.

The invention provides an improved device and method for suturing openings and incisions through tissue into a body cavity of a patient. Most often, the device and method will be used for suturing percutaneous penetrations where the suture may be anchored in the underlying fascia layer. The device and method may also be used for suturing penetrations in internal body organs and structures. The device and method will find particular use in minimally invasive surgery including laparoscopic, endoscopic and arthroscopic surgeries.

A first embodiment of a surgical suturing device 10 constructed in accordance with the principles of the present invention as illustrated in FIG. 1A–1D. The suturing device 10 includes shaft 13 having a handle 15 at its proximal end and a needle assembly 17 at its distal end. The needle assembly 17 includes an inverted needle 22 having a sharpened proximal tip 25 and is connected to the shaft 13 by a lateral segment 20. A pair of axially spaced-apart apertures 27 and 28 are formed in the needle 22 immediately distal to the sharpened proximal tip 25. First end 30 and second end 31 of the length of suture 35 are secured within the first aperture 27 and second aperture 28, respectively.

The suturing device 10 may be formed from a single length of stainless steel or other medically acceptable needle stock. The device 10 may be constructed simply by bending needle stock into the illustrated geometry. Typically, the overall length of the device will be in the range from 10 cm to 60 cm, preferably from 25 cm to 30 cm, with the needle 22 having a total length from the distal end of the device to the proximal tip 25 of the needle in the range from 1 cm to 8 cm, preferably from 3 cm to 5 cm. The needle will usually be oriented parallel to the axis of shaft 13 and be laterally spaced-apart therefrom by a distance in the range from 3 mm to 15 mm, preferably from 5 mm to 10 mm.

It will be appreciated, however, that the geometry of the needle assembly 17 may vary and that the particular suture anchor(s) provided on the needle may differ. For example, FIG. 1A illustrates a J-shaped needle assembly 17a having a pair of suture-receiving slots 27a and 27b. The slots may be machined into the side of the needle, e.g., by electrical discharge machining methods or by stamping.

FIG. 1B illustrates a second alternative needle assembly 17b having a V-shaped geometry. While the inverted needle 22b will not be parallel to the axis of shaft 13b, the inclined needle orientation may be useful in certain procedures.

Yet a third alternative of a needle assembly 17c is illustrated in FIG. 1C. Needle assembly 17c includes a straight lateral element 20c joining shaft 13c to inverted needle 22c. Needle 22c includes a single aperture 27c located just distally of the sharpened proximal tip 25c. Suture ends 30 and 31 are crossed within the aperture 27c so withdrawal of the suture end 30 will not accidently dislodge the second end 31. It should be appreciated, of course, that other measures could be taken for isolating the suture ends within a single aperture. The primary requirement of the present invention is that the suture ends be secured to the inverted needle just distally of its sharpened proximal tip in an manner so that each suture end may be removed separately from the needle without dislodging the other suture end. Any design which achieves that objective would be suitable for the anchor(s) of the present invention. Such a design allows the needle to be repeatedly passed through tissue without having to reload suture onto the needle.

FIG. 1D illustrates a needle assembly 17d having a curved profile, similar to assemblies 17 and 17a, and including a single aperture 27d having suture ends 30 and 31 crossed therein.

A second embodiment 40 of a device according to the invention is depicted in FIGS. 2, 3A and 3B. FIG. 2 provides a top view of the device, FIG. 3A is a side view showing a shield 43 extended distally to expose sharpened tip 25d of 17d, and FIG. 3B is a side view with shield 43 retracted to cover the sharpened tip 25d. For convenience, elements in FIGS. 2, 3A, 3B, and 4 which are analogous to elements of the device 10 of FIG. 1 will be given identical reference numbers with the suffix d.

As can be seen in these views, the device 40 comprises a shaft 13d fitted with a handle 15d, and a needle assembly 17d comprising a lateral section 20d, an inverted needle 22d and the sharpened proximal tip 25d. Like the first embodiment 10 depicted in FIG. 1, the second embodiment has two spaced-apart anchors, i.e. apertures 27d and 28d, disposed immediately distal to the sharpened proximal tip 25d of the needle 22d.

Unlike the embodiment of FIG. 1, however, the second embodiment includes shield 43 slidably mounted on the shaft 13d. Shield 43 is connected by means of a link 45 to a slide 48 so that the shield may be retracted and extended by manual actuation of the slide 48 by the surgeon. Shield 43 is movable between a first position in which the sharpened proximal tip 25d of the needle 22d is exposed (FIG. 3A) and a second position in which the sharpened proximal tip is covered (FIG. 3B).

The device 40 further includes a set of ridges or serrations 65 on link 45 of shield 43. These serrations provide a visual and tactile indicator to the surgeon to indicate which side of the device the suture is loaded on (in order to permit quick identification of the side from which to remove the suture). The suture ends are preferably threaded into and withdrawn from the side of the hook on which the indicator is located.

Usually, the suture 35 will be preloaded onto the suturing device 40, and the construction of device and suture placed in a sterilized pack. A particular advantage of the present invention is that the fabrication cost is sufficiently low so that the device may be disposable. The device, however, may be reusable, in which case the needle 22d will have to be rethreaded with suture as illustrated.

The individual parts of the device may be formed of a variety of materials having suitable properties. For example, the needle assembly 17d and shaft 13d may be formed of surgical stainless steel. Shield 43, link 45 and slide 48 can be made of a medical grade polycarbonate plastic such as LEXAN® (General Electric Plastics). Finally, handle 15d can be made of a medical grade ABS plastic such as CYCOLAC® (General Electric Plastics). For reusable products, it is best if all components can withstand high temperatures to permit autoclaving. Suitable autoclavable materials include stainless steel.

It will be appreciated that the geometry of the needle assembly 17d may be varied as described above in connection with the needle assembly 17 of the surgical suturing device 10. That is, the needle 22d will preferably be straight, but may have some degree of curvature or other deviation so long as it does not inhibit tissue penetration and withdrawal according to the method of the present invention, as described hereinafter. The needle 22d will also usually be oriented parallel to the shaft 13d, but may deviate so long as the ability to utilize the needle is not significantly compromised. Similarly, a wide variety of suture anchor(s) may be used together with or in place of the apertures 27d and 28d.

In addition to variations in the structure of needle assembly 17d, the structure of the needle shield 43 may also be varied in any manner consistent with its primary requirement, i.e. the ability to selectively cover the sharpened proximal tip 25d so that the tip may be exposed when tissue is being penetrated to introduce suture and may be covered when it is necessary to withdraw the device 40 to remove the needle assembly 17d through the penetration without accidental needle penetration.

An exemplary method for suturing with either the first device (FIG. 1) or the second embodiment (FIGS. 2, 3A and 3B) is illustrated in FIGS. 4–9. Note that these figures depict the method as performed with the second embodiment 40.

Figure 4:
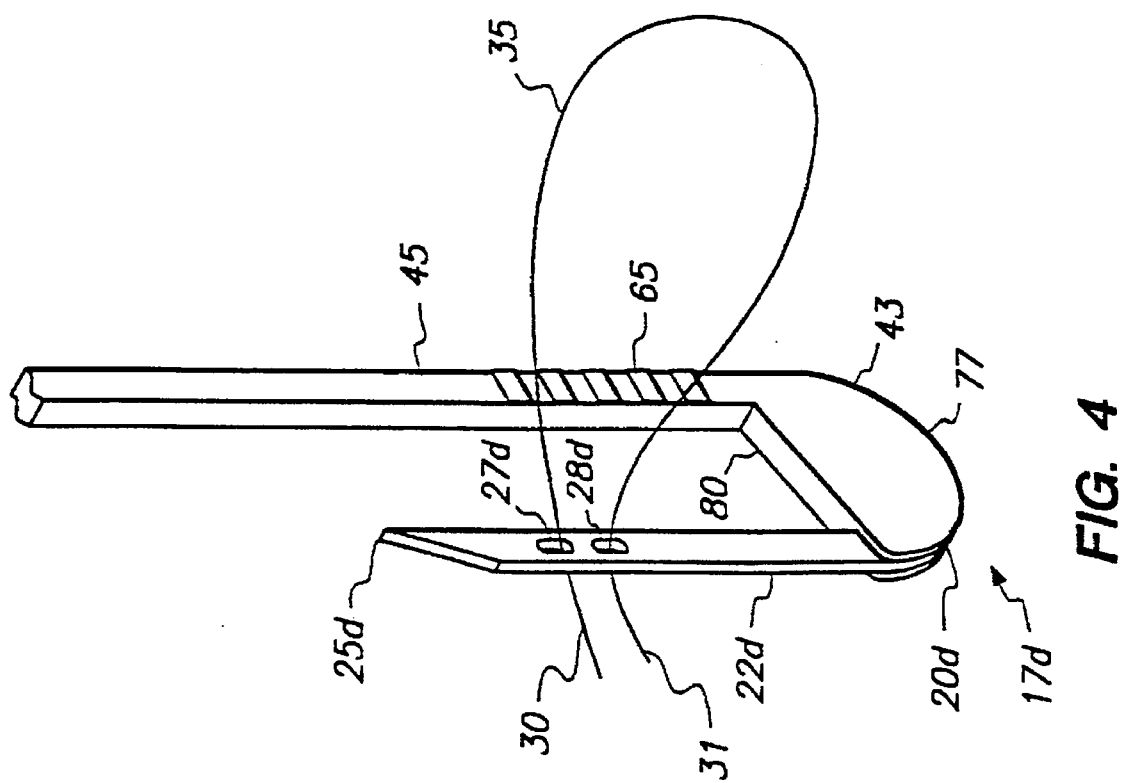

With shield 43 extended as depicted in FIG. 4, i.e. with sharpened tip 25d of needle assembly 17d exposed, suture material 35 is loaded (if necessary) into the device by threading first and second ends 30 and 31 through eyes 27d and 28d on needle 22d. After suture material 35 is loaded into needle 22d, the hook and the suture material are inserted into a body cavity 50 through a percutaneous penetration 25 in tissue 54 as illustrated in FIG. 5. Optionally, the shield 43 may be retracted proximally to cover the needle tip 25d during insertion. Tissue 54 comprises three layers, the peritoneum 56, the fascia 58, and the subcutaneous layer 60.

Figure 6:
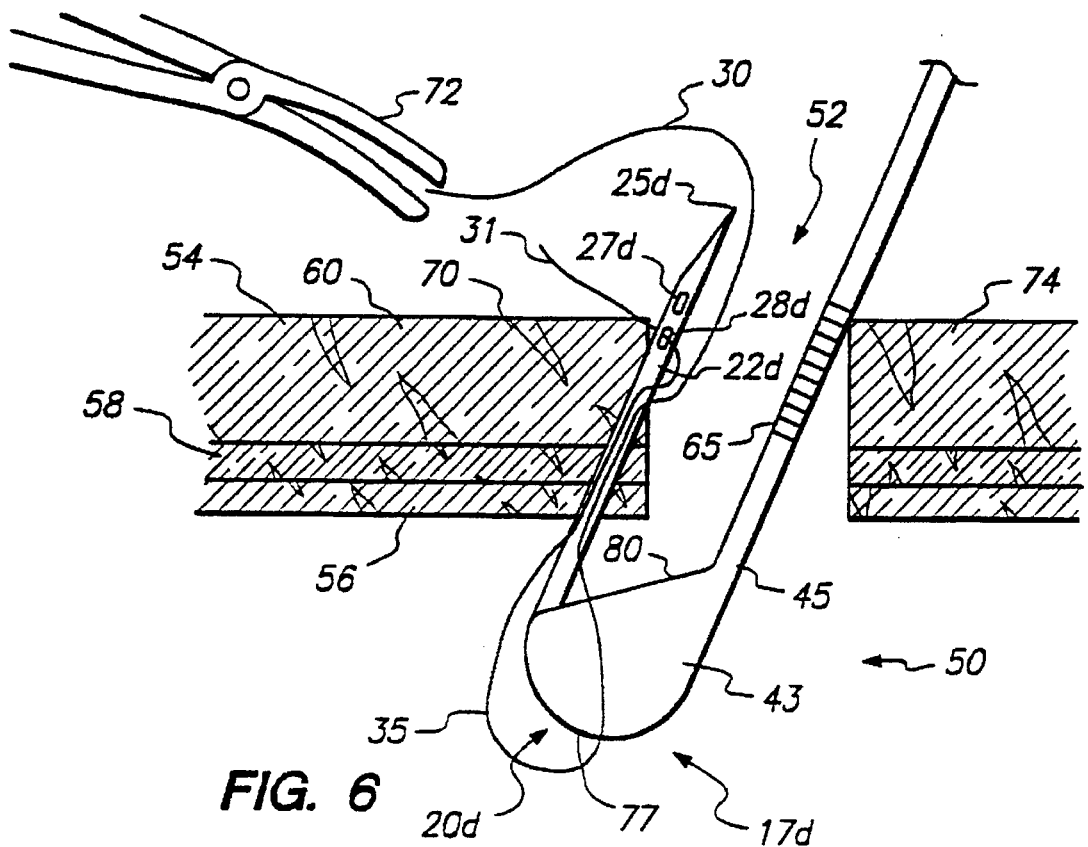

Referring now to FIG. 6, the sharpened proximal tip 25d of needle 22d is pulled up to create a first penetration on a first side 70 of the percutaneous penetration 52. The needle 22d is drawn up through peritoneum 56, fascia 58, and at least a portion of subcutaneous layer 60. This draws both ends 30 and 31 of suture material 35 out of body cavity 50. The first end 30 is then removed from the first eye 27d and secured with a clamp 72.

Figure 7:
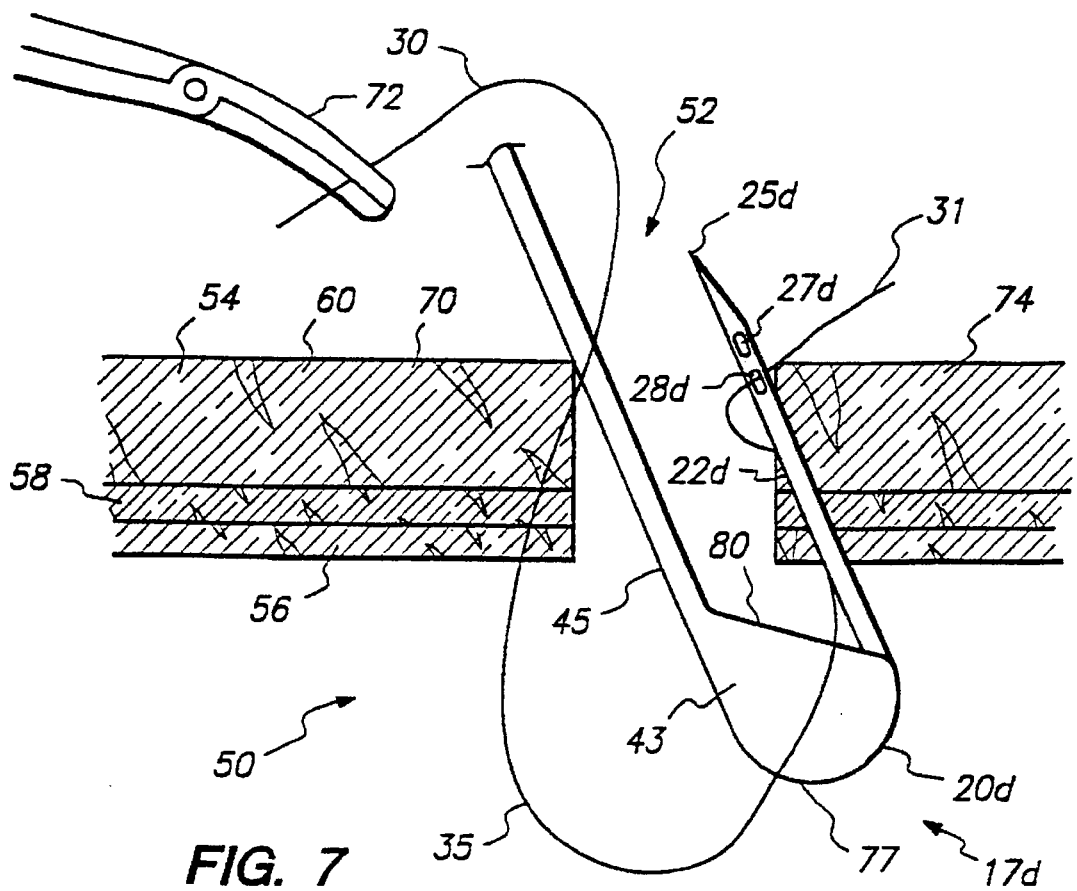

Referring to FIG. 7, the distal end of the device including needle assembly 17d is then pushed back into the body cavity through the first penetration, rotated to a second side 74 of penetration 52, and pulled back out of the body cavity to form a second penetration through at least a portion of the second side of the tissue including fascia 58. The second end 31 of suture material 35 should be pulled through peritoneum 56, fascia 58 and at least a portion of subcutaneous layer 60.

Figure 8:
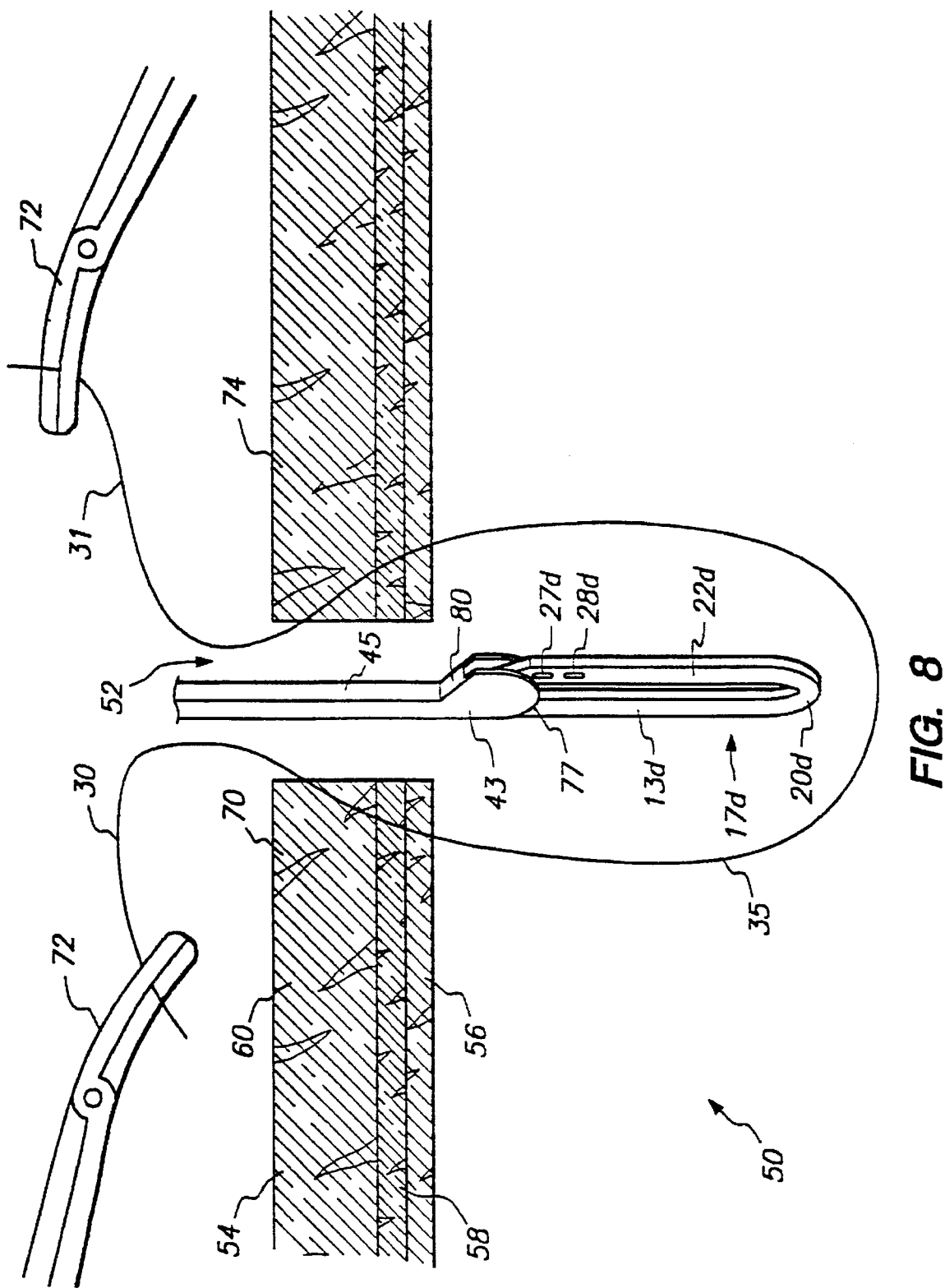

As depicted in FIG. 8, the second end 31 of the suture material is removed from the needle 22d and clamped, and the needle is pushed back through the second puncture into the body cavity 50. Shield 43 is then shifted to cover the sharpened tip 25d of the needle 22d so that the needle may be withdrawn safely from the body cavity through the percutaneous penetration without danger of puncturing or snagging the tissue at the sides of the penetration.

Figure 9:
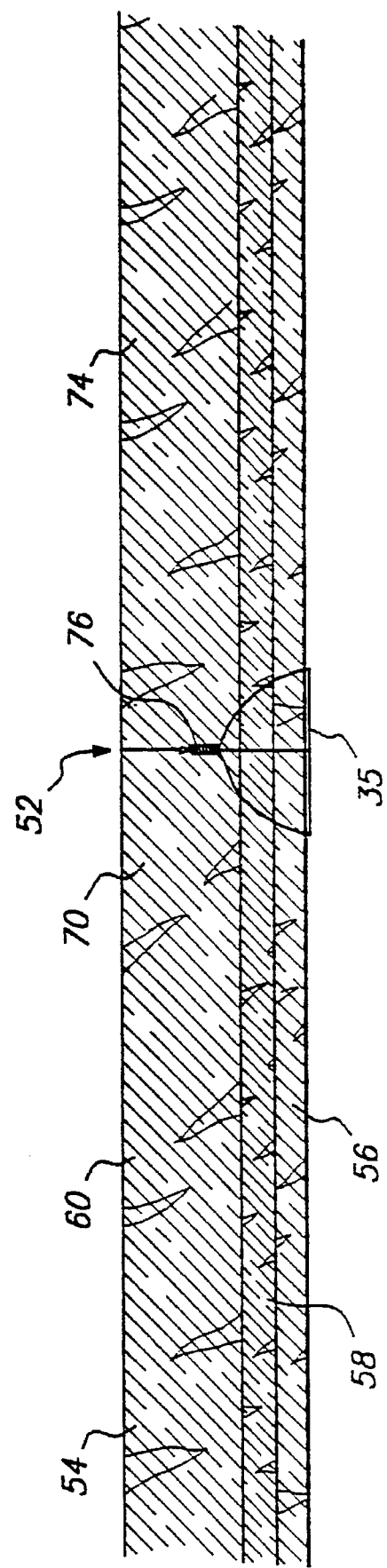

Finally, as depicted in FIG. 9, the ends of suture material 35 are drawn tight to close the incision. A knot 76 is tied by the surgeon to secure the ends of the suture, and the remaining loose ends are clipped and discarded. The penetration will thus be able to heal quickly with minimum scarring since the suturing penetration beneath the skin. By drawing the suture ends back through the sides of the tissue, i.e., through the sides of the subcutaneous layer as depicted in these figures, rather than completely through the top skin layer of the tissue, the penetration may be closed without the deformation and surface scarring that might otherwise result. The suture should be drawn completely through the fascia layer, however, as this tough and fibrous layer of tissue makes a good anchor for a high strength suture, preventing herniation.

Referring back to FIGS. 3A and 3B, the shield 43 of the depicted embodiment is provided with surfaces providing functional advantages during use of the device. Referring specifically to FIG. 3A, when shield 43 is extended, a bottom surface 77 of the shield presents a curved leading edge which minimizes the risk of trauma as the needle assembly 17d is inserted though the penetration into the patient's body cavity (see FIG. 5). Of course, other tapered and/or blunt geometries could be selected for the leading edge to minimize the risk of trauma, as just described. Thus, with the protective shield 43 extended distally, the lateral element 20d will be covered so that its geometry is not critical.

Referring now to FIG. 3B, shield 43 may be further provided with an inclined or canted top surface 80. When the shield is in its retracted position covering the hook, top surface 80 slopes away from shaft 13. This is advantageous since it reduces snagging and facilitates the smooth withdrawal of the device from the patient's body cavity near the end of the procedure (see FIG. 8).

Figure 10:
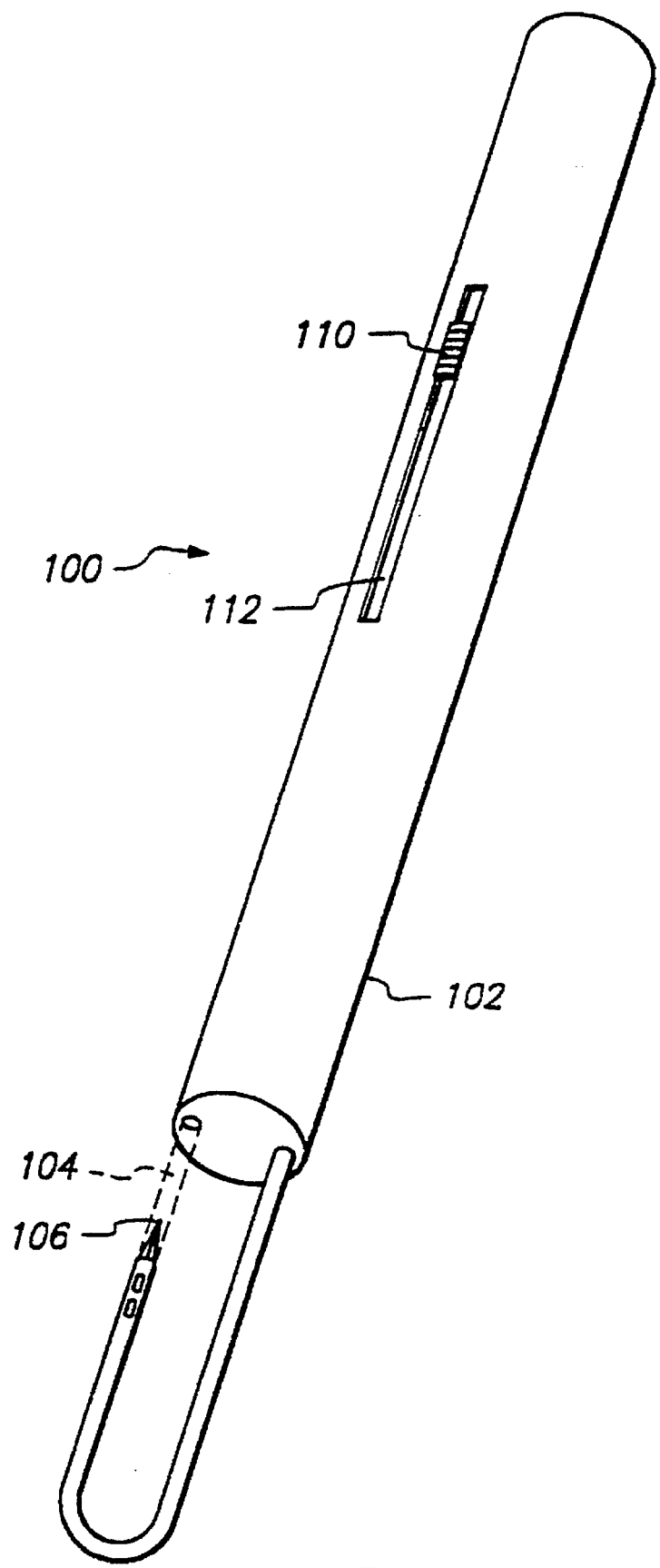
FIG. 10 illustrates a third embodiment of a suturing device constructed according to the present invention.

FIG. 10 illustrates an alternate embodiment 100 of the device of the present invention. The device 100 differs from the previous embodiments in several respects. First, a cylindrical body 102 is sized so that it can be introduced through a conventional trocar, typically having a nominal outer diameter of 5 mm to 18 mm, corresponding to conventional trocar lumen sizes. By providing such a cylindrical body 102, the trocar could be removed over the device 100, and the device body 102 will substantially occlude the tissue puncture site, limiting bleeding and maintaining insufflation. It would further be possible to reintroduce the trocar over the device 100 to regain access to the puncture site for any reason.

A second modification in device 100 is a shield 104 which is extended distally to cover tip 106 of needle assembly 108, as illustrated in broken line. The shield 104, in turn, is actuated by thumb slide 110, which is recessed in a slot 112 formed in the side of body 102. In this way, the slide 112 does not interfere with introduction of the device 100 through a trocar.

Other possible modifications of the device include a collar or ring which may be mounted about the shaft of any of the devices heretofore described and illustrated. The collar or ring could be formed to engage and seal against a tissue puncture site to staunch bleeding and/or maintain insufflation.

A further exemplary embodiment of the suturing device of the present invention includes a suturing device having a positionable needle that can radially or laterally be moved between an open or exposed position and a closed or protected position. This embodiment allows the suturing device to be either inserted into or withdrawn from a patient with the needle being in a protected position. Preferably, this is accomplished by protecting the needle in a recess of a shaft of the suturing device. When the shaft is inserted into the patient, the needle is flush with or within the walls of the shaft allowing for easy and safe insertion of the device into the patient. When the device is inside the patient, the needle is moved outward to an exposed position so that the suture may be applied. Usually, the needle will be held in an axially parallel orientation at all times, but may also be pivotally mounted to move between the exposed and retracted positions. Once the suture is applied, the needle is once again retracted to the closed position where the needle is protected by the shaft, and the device is safely and easily removed from the patient.

The needle is moved between the exposed and retracted positions by a mechanism which connects the needle to a location at or near a distal end of the shaft. The mechanism can easily be actuated by a surgeon while the device is within the patient. The mechanism can be any of a variety of know mechanical linkages, including pivotal connections, parallel bar linkages, and the like. A preferred linkage is a rotatable arm which is connected at or near the distal end of a rod running axially through the shaft. The opposite end of the rod is attached to a knob. When the knob is rotated, the rod moves the needle outwardly from the shaft to the exposed position. After the suture is applied, the knob is rotated in the opposite direction to place the needle in the recess of the shaft.

In another aspect, the needle can be locked in the open position. This prevents the needle from closing when applying the suture. The needle can be locked in place by frictional forces created when the component parts of the needle assembly contact the shaft. To unlock the shaft, the knob can be turned with sufficient force to overcome the frictional forces between the needle assembly and the shaft. Alternatively, the needle can be locked by a locking mechanism that is conveniently actuable from the proximal end of the device to allow the surgeon to lock the needle when desired.

In a further aspect, each longitudinal half of the shaft can be colored with a different color. Coloring of each half provides a convenient reference to the user to help insure that the suture is both loaded and removed from the same side of the needle.

Referring to FIGS. 11A and 11B, an exemplary embodiment of a suturing device 200 will be described. The suturing device includes a shaft 202. As described in detail hereinafter, the shaft 202 includes a lumen 226 (shown in FIGS. 13B–13D) for receiving a rod 206. Alternatively, the rod 206 can be rotatably attached to the outer periphery of the shaft 202.

For ease of insertion into the patient, the shaft 202 is cylindrical in geometry. However, the shaft 202 can include other geometries suitable for insertion into an incision and which can provide a protected area to receive the needle 210. The cylindrical geometry of the shaft also assists when inserting or removing a trocar over the shaft 202. The diameter of the shaft 202 is preferably sized to seal in the pneumoperitoneum during suturing of the wound.

At a distal end of the rod 206 is an arm 208 which connects the rod 206 to a needle 210 to form an inverted needle as previously described. Attached to the proximal end of the rod 206 is a knob 212 which is used to rotate the rod 206. The rod 206, arm 208, needle 210, and knob 212 are used together to radially deploy or retract the needle 210 between an open or exposed position (as shown in FIG. 11A) and a closed or protected position (as shown in FIG. 11B) and will be described in detail hereinafter.

The shaft 202 and knob 212 are preferably constructed of a medical grade polycarbonate plastic such as LEXAN® (General Electric Plastics). Use of such materials allows for convenient molding of the shaft 202 and knob 212 into the desired shape. Molding also allows for easy formation of a vertical recess 214 used to receive the needle 210 when in the protected position. The recess 214 is constructed so that when the needle 210 is in the protected position, the needle 210 will be substantially flush with or recessed below the outer circumference of the shaft 202. This allows for device 200 to be inserted into or withdrawn from the patient without catching or snagging surrounding tissue. The shaft 202 also has a horizontal recess 215 for receiving the arm 208 when the needle 210 is in the closed position as described hereinafter.

At the proximal end of the shaft is a resilient button 216 used to lock the needle in the open position. This feature provides additional safety by insuring that the needle 210 will remain in the open position while the suture is being applied. The button 216 is resilient in that it is biased in a proximal axial direction relative to the shaft 202. When the knob 212 is rotated, the outer diameter of the knob 212 will pass the button 216 allowing the button 216 to move in the proximal direction beyond a distal end of the knob 212. The button 216 remains biased in this position until depressed, thereby preventing the knob 212 from returning to the closed position. To close the needle 210, the button 216 is simply depressed, e.g., by applying force with a finger, to lower the button 216 below the distal end of the knob 212 and rotating the knob 212 to the closed position.

As shown in FIGS. 12A–12C, the knob 212 is preferably cylindrical to conform to the outer geometry of the shaft 202, but can conveniently be fashioned in any geometry as long as the knob 212 can conveniently rotate the rod 206. Optionally, the knob 212 contains ridges 218 as shown in FIG. 12C to provide a convenient gripping surface on the knob 212.

The knob 212 is rigidly connected to the rod 206 so that when the knob 212 is rotated, a torque is transferred to the rod 206. The rod 206 in turn is rigidly attached to the arm 208 and the needle 210. When the knob 212 is rotated, the needle 210 moves in an arc relative to the rod 206. Since the rod 206 is attached to a wall of the shaft 202, the needle 210 moves radially outward from the shaft 202 when the knob 212 is rotated. The rod 206, arm 208 and needle 210 can be constructed of stainless steel or other medically acceptable rigid material and in the case of metals can be joined by welding, crimping, peening, and the like. Alternatively, the rod 206, arm 208, and needle 210 can be formed as in integral unit from the same piece of material.

The needle 210 includes a sharpened proximal tip 220 and a pair of spaced-apart apertures 222 and 224. A length of suture is received within the two apertures 222 and 224 as described hereinafter. The needle 210 can be recessed in the areas of the apertures 222 and 224 to assist in removing the suture. When the suture is placed through the apertures 222 and 224 and pulled tight, the recess provides a space between the suture and the needle 210 so that the suture can be grasped for removal from the needle 210. Alternatively, the needle 210 can be entirely straight, or have other geometries as required for the specific application.

The needle 210 includes at least two apertures so that a suture can be loaded through both apertures. This eliminates the need to reload the needle with suture between stitches. After one stitch is made, one end of the suture can be removed from one of the apertures. A second stitch can then be made because the suture is still loaded on the needle through the second aperture. Alternatively, the needle 210 could be provided with more than two apertures so that more than one suture can be loaded onto the needle 210. This allows for multiple suturing without removing the device 220 from the wound to load additional sutures.

Figure 21:
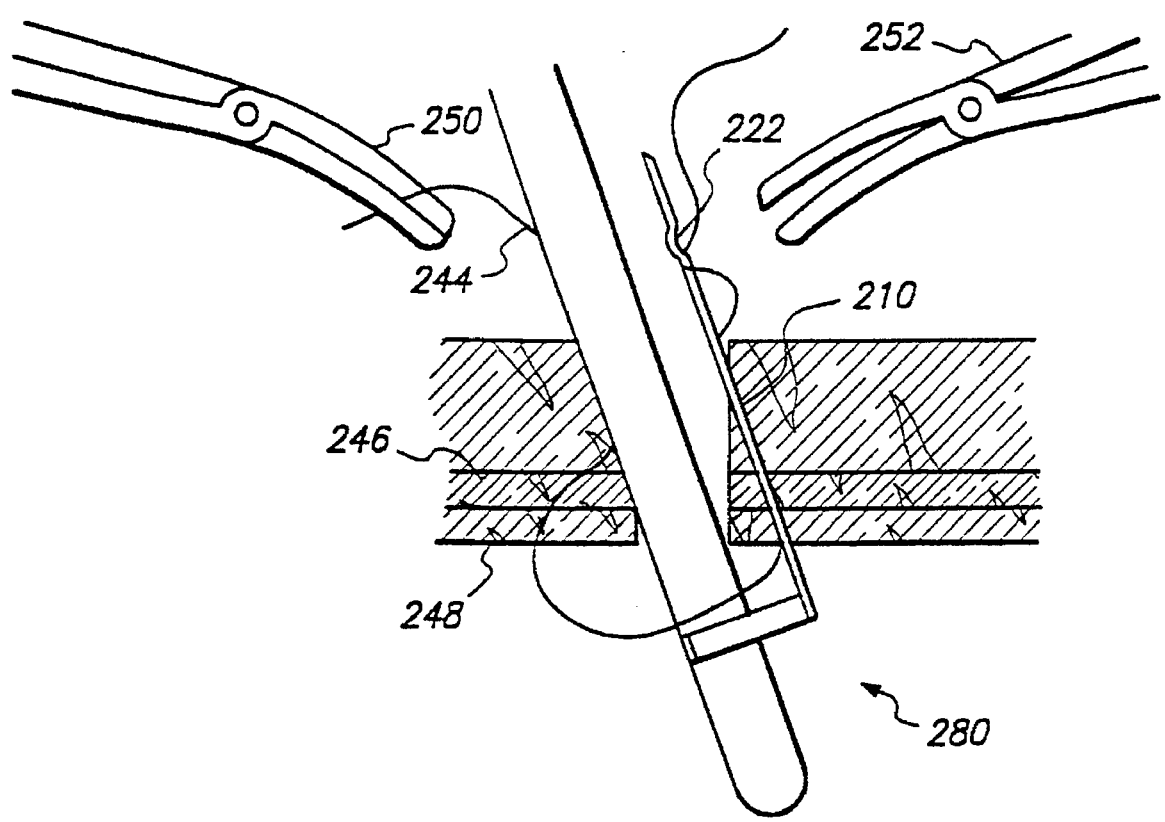

The arm 208 is straight for manufacturing convenience. Alternatively, the arm 208 can be curved as shown in FIG. 21. If the arm 208 is straight, the horizontal recess 215 of the shaft 202 will be large enough to receive the arm 208 when the needle is retracted to the closed position. Alternatively, if the arm 208 is curved, the recess 215 need only be large enough to ensure that the arm 208 is substantially flush with the outer geometry of the shaft 202 when the arm 208 is in the closed position.

Figure 13:
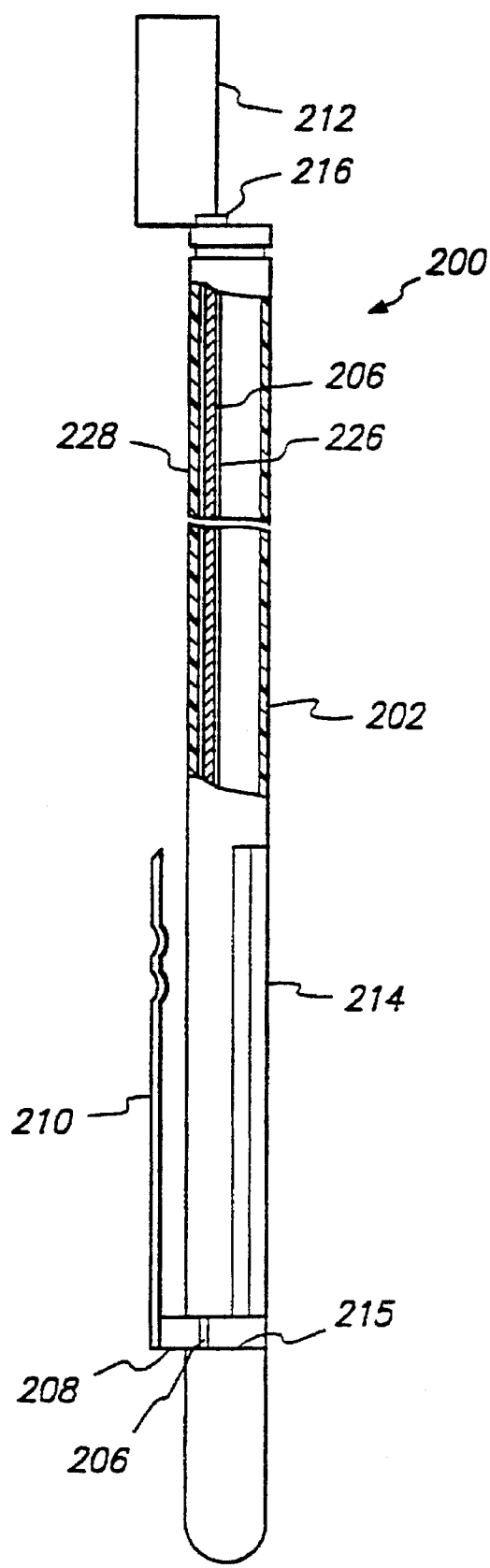
FIGS. 13 and 14 illustrate a cut-away view showing the interior of the suturing device of FIGS. 11A and 11B.
Figure 14:
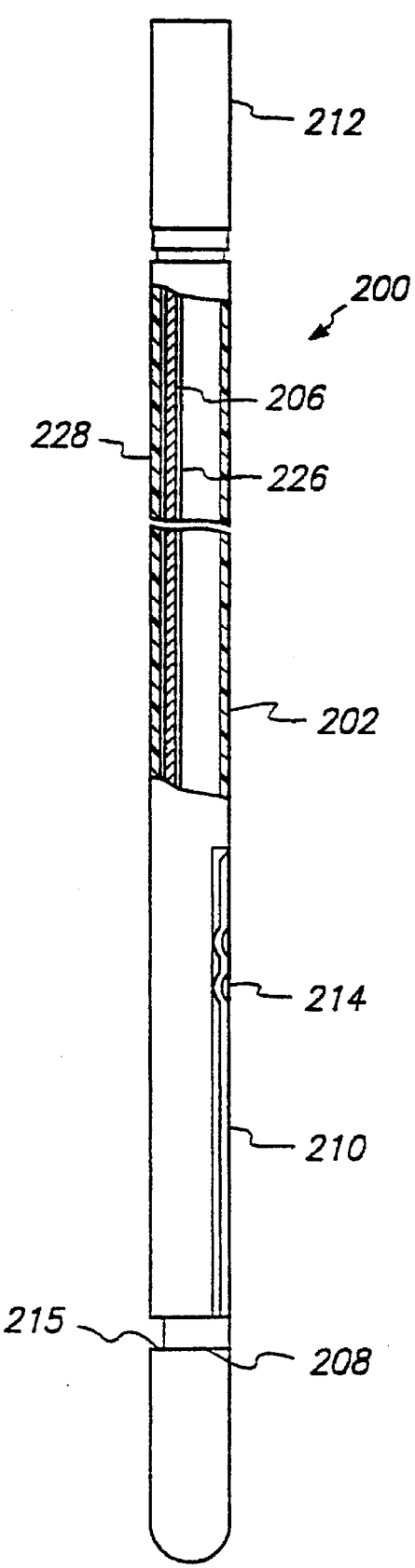
Figure 15:
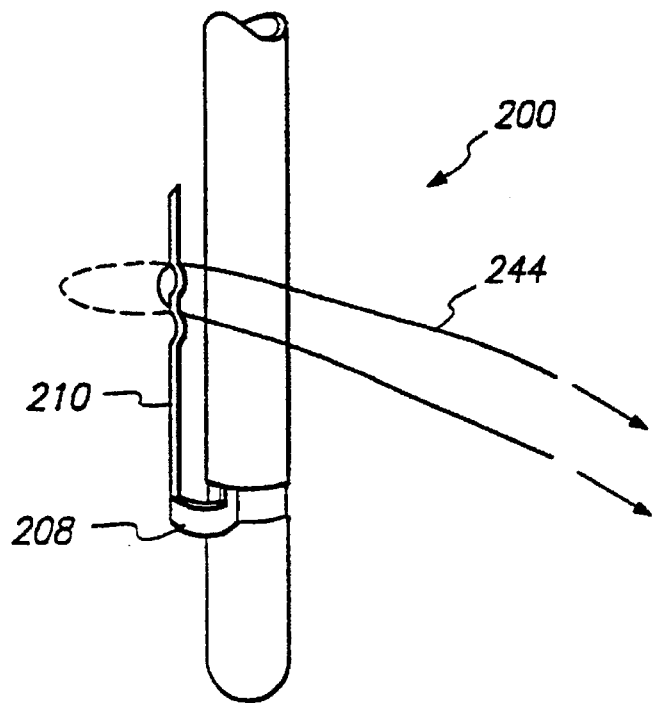
FIGS. 15–18 illustrate use of the device of FIGS. 13 and 14 in an exemplary method for using the device according to the present invention.

Turning to FIGS. 13 and 14, the construction of the suture device 200 will be described in greater detail. The shaft 202 contains a lumen 226 for receiving the rod 206. The shaft 202 is substantially hollow and the lumen 226 is formed in a wall 228 of the shaft 202. In order to place the rod 206 in the lumen 226, the shaft 202 is preferably fabricated in two halves which are joined together. The halves can be joined in any manner so long as the rod 206 can rotate within the lumen 226.

Both halves contain a cylindrical recessed portion which forms the lumen 226 when the halves are joined. The rod 206 is placed in the recessed portion before the halves are joined. The button 216 is formed at the proximal end of one of the halves. The button 216 is preferably a piece of rigid material protruding from the proximal end of the shaft 202. The button 216 is integrally formed with the shaft 202 and is biased in the proximal direction. When the knob 212 is rotated to the open position, the button 216 extends beyond the distal end of the knob 212 to lock the knob 212 in the open position. To close the needle, the button 216 is depressed allowing the knob 212 to pass the button 216 and be rotated back to the closed position.

Instead of using the button 216 as a locking mechanism, any suitable locking mechanism can be used to maintain the needle in the extended position. For example, a releasable latch can be provided at the distal end of the knob 212 that can latch the proximal end of the shaft 202 when the knob is rotated to the open position. Alternatively, the needle 210 can be locked in the open position by a frictional force created between the elements of the needle assembly (as shown in FIG. 12A) and the shaft 202. Some of the frictional forces occur between the rod 206 and the lumen 226. The rod 206 or the lumen 226 can be sized appropriately so that the tolerance between the rod 206 and lumen 226 is sufficient to provide the necessary locking force.

When the rod 206 is placed in the lumen 226, the knob 212 rests on the proximal end of the shaft 202 while the distal end of the rod 206 rests in the recess 215. With this configuration, the needle 210 can be moved between the extended and retracted positions by merely turning the knob 212. The horizontal recess 215 is used to receive the arm 208 when in the closed position.

FIGS. 15–18 illustrate an exemplary method for using the suture device 200. Initially, the knob 212 (as shown in FIG. 13) is rotated as previously described to place the needle 210 in the exposed position. This exposes apertures 222 and 224. A suture ligature 244 is then loaded through the apertures 222 and 224 from the same side, i.e. each end of the suture exits the apertures 222 and 224 from the same side of the needle 210. The suture 244 is adjusted so that each end is approximately equal in length, and the suture 244 is pulled tight against the needle 210. The button 216 (as shown in FIG. 13) is then pressed to unlock the needle 210 allowing the knob 212 to be rotated to close the needle 210. Alternatively, if no button is provided, the knob 212 can be torqued with a sufficient force to overcome the frictional forces and rotate the needle to the closed position.

Once in the closed position, the device 200 is inserted into the patient through a cannula. Subsequently, the cannula is removed from the patient by sliding the cannula over the device 200. Alternatively, the device 200 can be introduced directly through a trocar incision in the patient.

Figure 16:
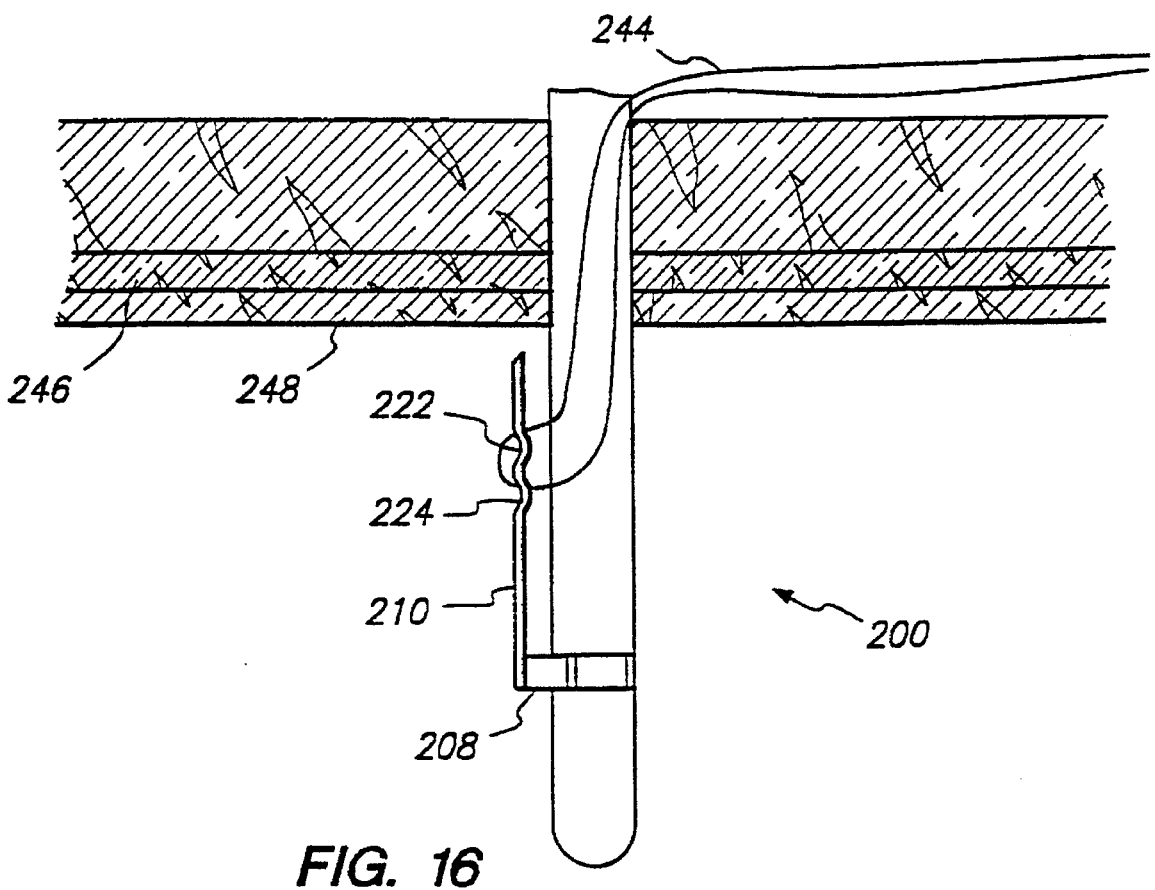

As shown in FIG. 16, after the device 200 is inside the patient, the needle 210 is moved to the exposed position and locked in place by rotating the knob 212. Preferably, this is done under direct visualization. The needle 210 is then advanced through the fascia layer 246 and subcutaneous tissue 248.

Figure 17:
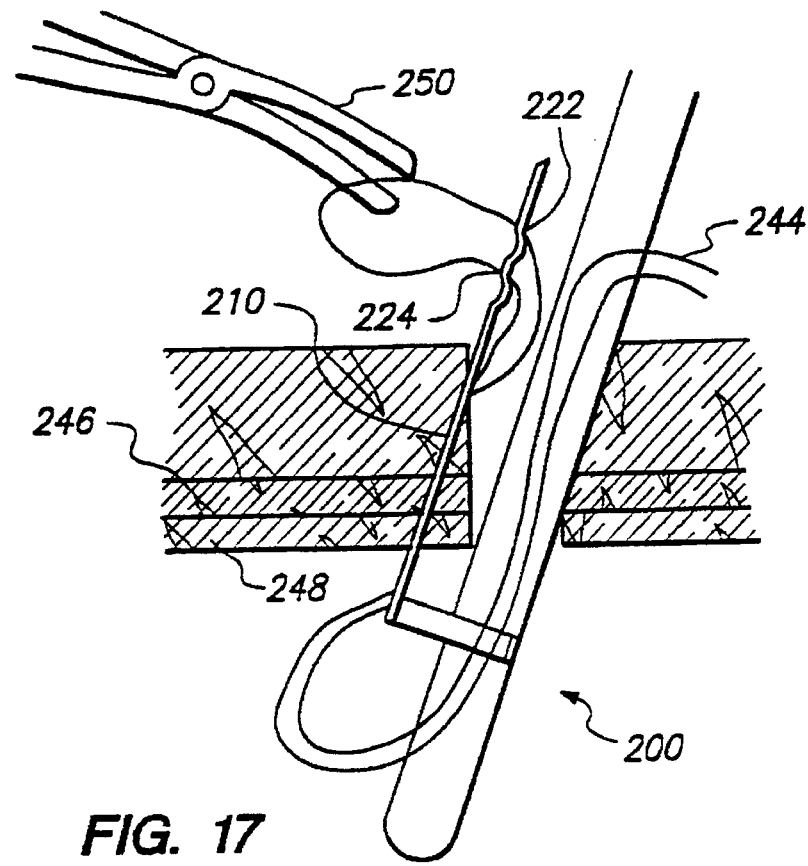
Figure 18:
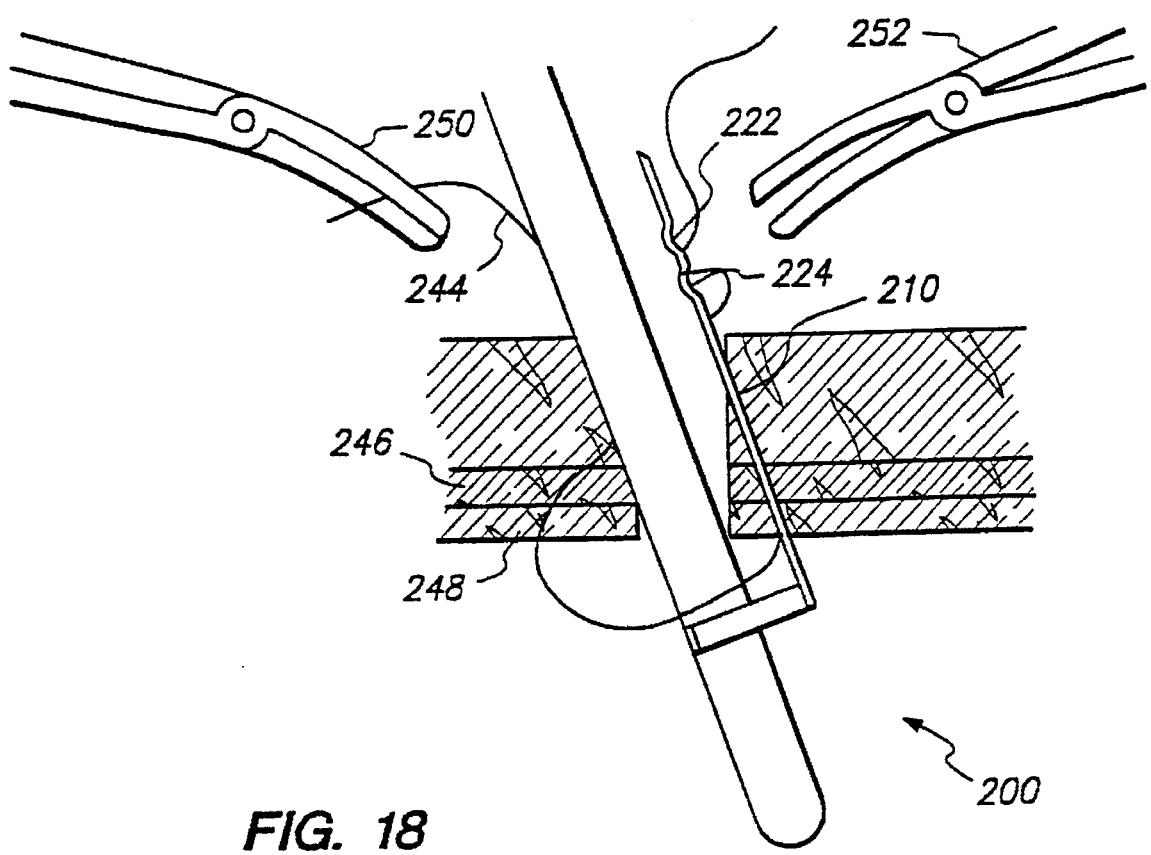

Once the needle 210 is outside the wound, one end of the suture 244 is removed from aperture 222 by pulling the suture 244 from the same side it was loaded as shown in FIG. 17. The removed end of the suture 244 is then secured with a clamp 250. The device 200 is then directed back towards the patient to remove the needle 210 from the fascia 246. Preferably, this is done under direct visualization. The device 200 is then rotated to the opposite side of the incision and the needle 210 is advanced through the fascia 246 and the subcutaneous tissue 248 as shown in FIG. 18. The remaining free end of the suture 244 is then removed from aperture 224 from the same side it was loaded into the aperture and secured with a clamp 252.

The device 200 is then redirected towards the patient to remove the needle 210 from the fascia 246. The needle 210 is then placed in the closed position by rotating the knob 212 and retracting the device 200 from the patient. The suture 244 is then secured with a standard surgeon's knot.

Figure 19:
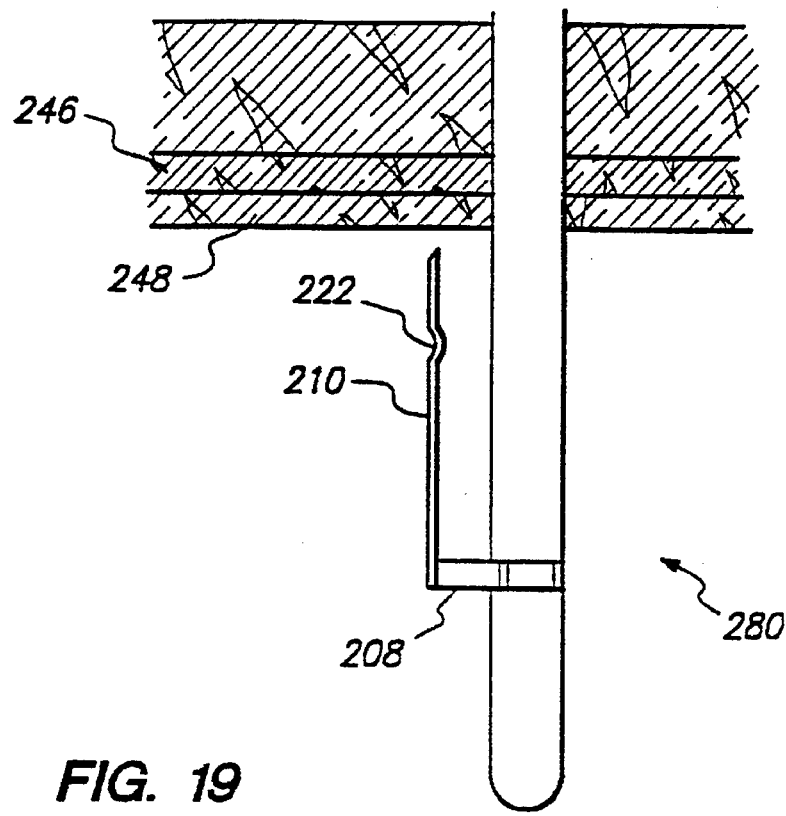
FIGS. 19–21 illustrate an exemplary suturing method according to the present invention.
Figure 20:
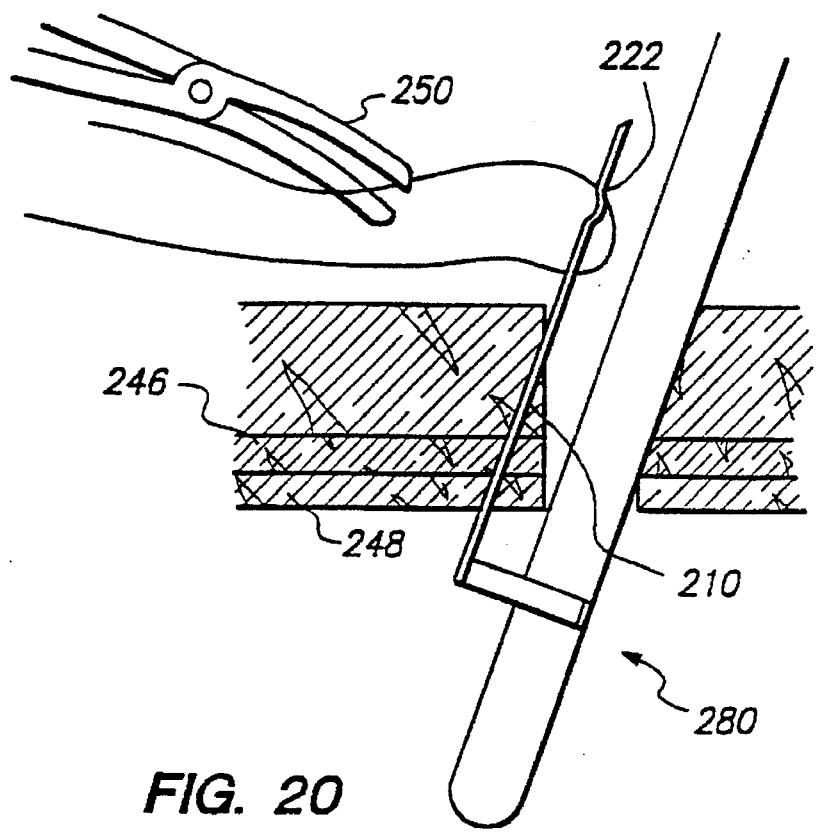

An exemplary suturing method as illustrated in FIGS. 19–21 will next be described. The method employs a suturing device 280 is that is essentially identical to the suturing device 200 except that the needle 210 includes only the aperture 222. For convenience of discussion, the suturing device 280 will be described using the same reference numerals used to describe the method illustrated in FIGS. 16–18. Initially, the device 280 (while the needle 210 is in the closed position) is inserted into the patient through a cannula. Subsequently, the cannula is removed from the patient by sliding the cannula over the device 280. Alternatively, the device 280 can be introduced directly through a trocar incision in the patient.

As shown in FIG. 19, after the device 280 is inside the patient, the needle 210 is moved to the exposed position and locked in place by rotating the knob 212. Preferably, this is done under direct visualization. The needle 210 is then advanced through the fascia layer 246 and subcutaneous tissue 248.

Once the needle 210 is outside the wound, one end of the suture 244 is directed through the aperture 222 and the suture 244 is adjusted so that both ends are approximately equal in length. One end of the suture 244 is then secured with a clamp 250 as shown in FIG. 20. The device 280 is then directed back towards the patient to remove the needle 210 from the fascia 246. Preferably, this is done under direct visualization. The device 280 is then rotated to the opposite side of the incision and the needle 210 is advanced through the fascia 246 and the subcutaneous tissue 248 as shown in FIG. 21. The remaining free end of the suture 244 is then removed from aperture 222 and secured with a clamp 252.

The device 280 is then redirected towards the patient to remove the needle 210 from the fascia 246. The needle 210 is then placed in the closed position by rotating the knob 212 and retracting the device 280 from the patient. The suture 244 is then secured with a standard surgeon's knot.

The present invention has been described in detail. However, modifications and variations may occur to those skilled in the art without departing from the principles of the claimed invention. Therefore, the scope of the invention should be determined primarily with reference to the appended claims, along with the full scope of equivalents to which those claims are entitled by law.

What is claimed is:

1. A surgical suture device comprising:
   an elongate shaft having a proximal end and a distal end;
   an inverted needle having a distal end and a sharpened proximal tip;

means located on the needle immediately distal to the sharpened tip for separately securing opposite ends of a length of suture thereto, wherein one end of suture can be removed from the needle without dislodging the other end of suture; and means for securing the needle near the distal end of the shaft so that the needle can move laterally between a protected position and an exposed position.

2. The device of claim 1, wherein the needle moves laterally between the protected and exposed positions by a laterally movable arm securing the needle to the shaft, the arm being laterally movable relative to an axis extending from the proximal end to the distal end of the shaft.

3. The device of claim 2, wherein the needle is held substantially parallel to the shaft.

4. The device of claim 1, wherein the means for securing the needle comprises a knob at the proximal end of the shaft, a rod attached to the knob and disposed axially within the shaft, and an arm attached to a distal end of the rod, wherein the distal end of the needle is secured to the arm so that rotation of the knob moves the needle between the protected and exposed positions.

5. The device of claim 4, further comprising locking means on the shaft for locking the needle in the exposed position.

6. The device of claim 5, wherein the locking means includes a resilient button at the proximal end of the knob, the button extending in a proximal axial direction above a distal end of the knob when the needle is in the exposed position.

7. The device of claim 4, wherein the arm is curved so that when the needle is in the protected position, the arm is substantially flush with the shaft.

8. The device of claim 1, wherein the shaft has a recess for receiving the needle when the needle is in the protected position.

9. The device of claim 1, wherein the means for securing the suture comprises a pair of spaced-apart anchors.

10. The device of claim 9, wherein the anchors are selected from the group consisting of apertures and slots.

11. The device of claim 9, wherein the needle includes a bend near the anchors.

12. The device of claim 11, wherein the bend is positioned between the pair of anchors to provide an area on the needle where the suture is disengaged from the needle.

13. An assembly comprising:

a length of a suture; and a surgical suturing device including an elongate shaft having a proximal end and a distal end, an inverted needle attached to the distal end of the shaft, the needle having a sharpened proximal tip, wherein at least two apertures are provided in the proximal tip for attaching the suture thereto, one of said at least two apertures disposed within 5 mm of the sharpened proximal tip for attaching one end of the suture thereto;

wherein the suture is disposed within the apertures with each end of the suture having an approximately equal length.

14. A method for suturing a tissue puncture site, said method comprising:

providing a suture device having an elongate shaft, an inverted needle at a distal end of the elongate shaft, and a length of suture removably attached to the needle near a sharpened proximal tip on the needle;

inserting the distal end of the device through the puncture site while the needle is recessed within the elongate shaft;

moving the needle laterally outward from the recessed position to an exposed position;

positioning the sharpened tip at a first target site on one side of the puncture site;

locking the needle in the exposed position;

drawing the needle outward through the tissue and removing a first end of the suture therefrom;

reinserting the distal end of the device through the puncture site and positioning the sharpened tip at a second target site on another side of the puncture site;

drawing the needle outward through the tissue and removing a second end of the suture therefrom; and securing the first and second suture ends to close the puncture site.

15. The method of claim 14, further comprising reinserting the distal end of the device through the puncture site after the second end of the suture has been removed from the needle, moving the needle laterally inward to the recessed position, and withdrawing the distal end of the device outward through the puncture site.

16. The method of claim 15, wherein a rod connected to the needle by an arm is rotated to retract or deploy the needle between the recessed and exposed positions.

17. The method of claim 15, further comprising unlocking the needle before retracting the needle from the exposed position to the recessed position.

18. The method of claim 15, wherein the puncture site is a percutaneous puncture site and the needle is drawn outward through the fascia layer and subcutaneous layer into the puncture site.

19. The method of claim 18, wherein the suture ends are secured within the puncture site beneath the skin.

20. The method of claim 15, further comprising visualizing the needle when deploying the needle from the recessed position to the exposed position, and when positioning the sharpened tip at the second target site.

21. The method of claim 14, wherein the suture device is disposed in a trocar and the tissue puncture site is in an internal body structure.

22. The method of claim 14, further comprising inserting the device through a cannula to insert the distal end of the device through the puncture site.

23. The method of claim 14, further comprising pulling equal lengths of the suture through the needle to secure the suture against the needle before inserting the device through the puncture site.

24. A method for suturing a tissue puncture site, said method comprising:

providing a suture device having an elongate shaft, an inverted needle at a distal end of the elongate shaft, and first and second ends of a length of suture removably attached to the needle near a sharpened proximal tip on the needle;

inserting the distal end of the device through the puncture site while the needle is recessed within the elongate shaft;

moving the needle laterally outward from the recessed position to an exposed position;

positioning the sharpened tip at a first target site on one side of the puncture site;

drawing the needle outward through the tissue and removing the first end of the suture therefrom;

reinserting the distal end of the device through the puncture site and positioning the sharpened tip at a second target site on another side of the puncture site;

drawing the needle outward through the tissue and removing the second end of the suture therefrom;

securing the first and second ends of the suture with a clamp after removing the ends from the needle; and securing the first and second suture ends to close the puncture site.

25. A method for suturing a tissue puncture site, said method comprising:

providing a suture device having an elongate shaft, an inverted needle at a distal end of the elongate shaft, and a length of suture removably attached to the needle near a sharpened proximal tip on the needle, wherein the length of suture is removably attached to the needle by placing the suture through a pair of apertures in the needle so that both ends of the suture exit the apertures at a common side of the needle;

inserting the distal end of the device through the puncture site while the needle is recessed within the elongate shaft;

moving the needle laterally outward from the recessed position to an exposed position;

positioning the sharpened tip at a first target site on one side of the puncture site;

drawing the needle outward through the tissue and removing a first end of the suture therefrom;

reinserting the distal end of the device through the puncture site and positioning the sharpened tip at a second target site on another side of the puncture site;

drawing the needle outward through the tissue and removing a second end of the suture therefrom; and securing the first and second suture ends to close the puncture site.

26. The method of claim 25, wherein the first and second ends of the suture are removed from the needle at the common side.

* * * * *